United States Patent
Saito et al.

(10) Patent No.: US 10,107,422 B2
(45) Date of Patent: Oct. 23, 2018

(54) FLEXIBLE TUBE AND INSERTION APPARATUS

(71) Applicant: OLYMPUS CORPORATION, Hachioji-shi, Tokyo (JP)

(72) Inventors: Kenichiro Saito, Tachikawa (JP); Takahiro Kishi, Yokohama (JP); Naoyuki Hoshi, Aizuwakamatsu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/602,827

(22) Filed: May 23, 2017

(65) Prior Publication Data

US 2017/0261136 A1    Sep. 14, 2017

Related U.S. Application Data

(63) Continuation of application No. PCT/JP2015/083801, filed on Dec. 1, 2015.

(30) Foreign Application Priority Data

Dec. 2, 2014   (JP) .................................. 2014-244360

(51) Int. Cl.
*A61B 1/00*   (2006.01)
*A61M 25/00*   (2006.01)
(Continued)

(52) U.S. Cl.
CPC .......... *F16L 11/10* (2013.01); *A61B 1/00064* (2013.01); *A61M 25/0054* (2013.01); *A61M 25/0147* (2013.01); *A61M 2025/015* (2013.01)

(58) Field of Classification Search
CPC .......... A61B 1/00064; A61B 1/00078; A61M 25/0054; A61M 25/0147;
(Continued)

(56) References Cited

U.S. PATENT DOCUMENTS 5,549,542 A  *  8/1996  Kovalcheck ......... A61B 1/0052
                                                        600/146
2009/0023989 A1*  1/2009  Honda ............... A61B 1/00133
                                                        600/106
(Continued)

FOREIGN PATENT DOCUMENTS

JP        S58-103431 A        6/1983
JP        2007-236472 A       9/2007
(Continued)

OTHER PUBLICATIONS

Feb. 23, 2016 Search Report issued in International Patent Application No. PCT/JP2015/083801.

(Continued)

*Primary Examiner* — Timothy J Neal
*Assistant Examiner* — Aaron B Fairchild
(74) *Attorney, Agent, or Firm* — Oliff PLC

(57) ABSTRACT

A flexible tube includes a helical tube including a closely-wound region and a sparsely-wound region, and an outer tube covering an outer side of the helical tube. The closely-wound region includes a closely-wound portion to which a tight contact force is applied, the tight contact force allowing adjacent parts of a wire member adjacent along the longitudinal axis to become a tight contact state, a sparsely-wound portion which is arranged at a proximal side of the closely-wound portion, and a change portion which is arranged at a proximal side of the sparsely-wound portion and, has the tight contact force between the adjacent parts on the proximal side rather than the distal side along the longitudinal axis reduced more than the tight contact force of the closely-wound portion.

10 Claims, 18 Drawing Sheets

(51) Int. Cl.
*A61M 25/01* (2006.01)
*F16L 11/10* (2006.01)

(58) Field of Classification Search
CPC ......... A61M 2017/00305; F16L 11/081; F16L 11/082; F16L 11/083; F16L 11/10; F16L 11/16
See application file for complete search history.

(56) References Cited

U.S. PATENT DOCUMENTS

| | | | | |
|---|---|---|---|---|
| 2013/0112457 | A1* | 5/2013 | Kitagawa | A61B 1/0056 174/68.3 |
| 2013/0144126 | A1* | 6/2013 | Iede | A61B 1/0055 600/139 |

FOREIGN PATENT DOCUMENTS

| | | |
|---|---|---|
| JP | 2013-090717 A | 5/2013 |
| JP | 2013-097327 A | 5/2013 |
| JP | 2014-113320 | 6/2014 |
| WO | 2013/168552 A1 | 11/2013 |
| WO | 2015/083644 A1 | 6/2015 |

OTHER PUBLICATIONS

Sep. 20, 2016 Office Action issued in Japanese Patent Application No. 2016-538823.
Jun. 15, 2017 Notification and Translation of IPRP issued in International Application No. PCT/JP2015/083801.

* cited by examiner

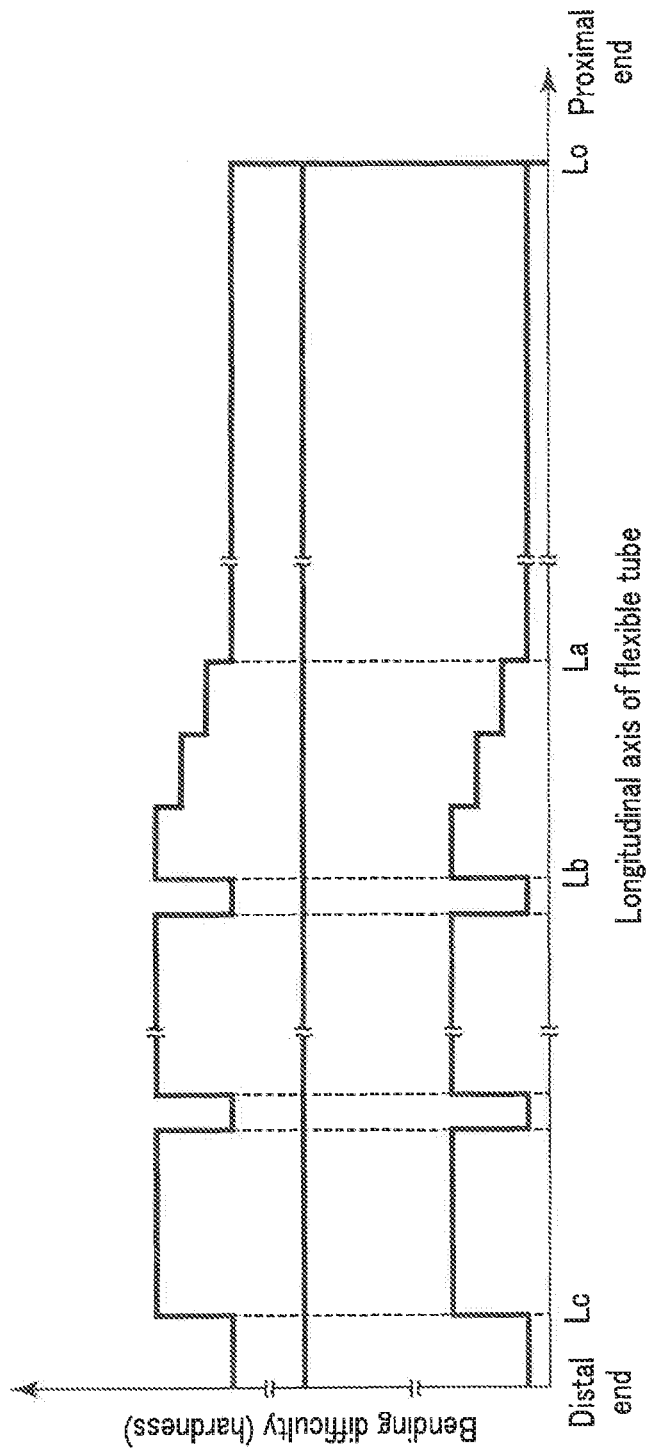
F I G. 4A

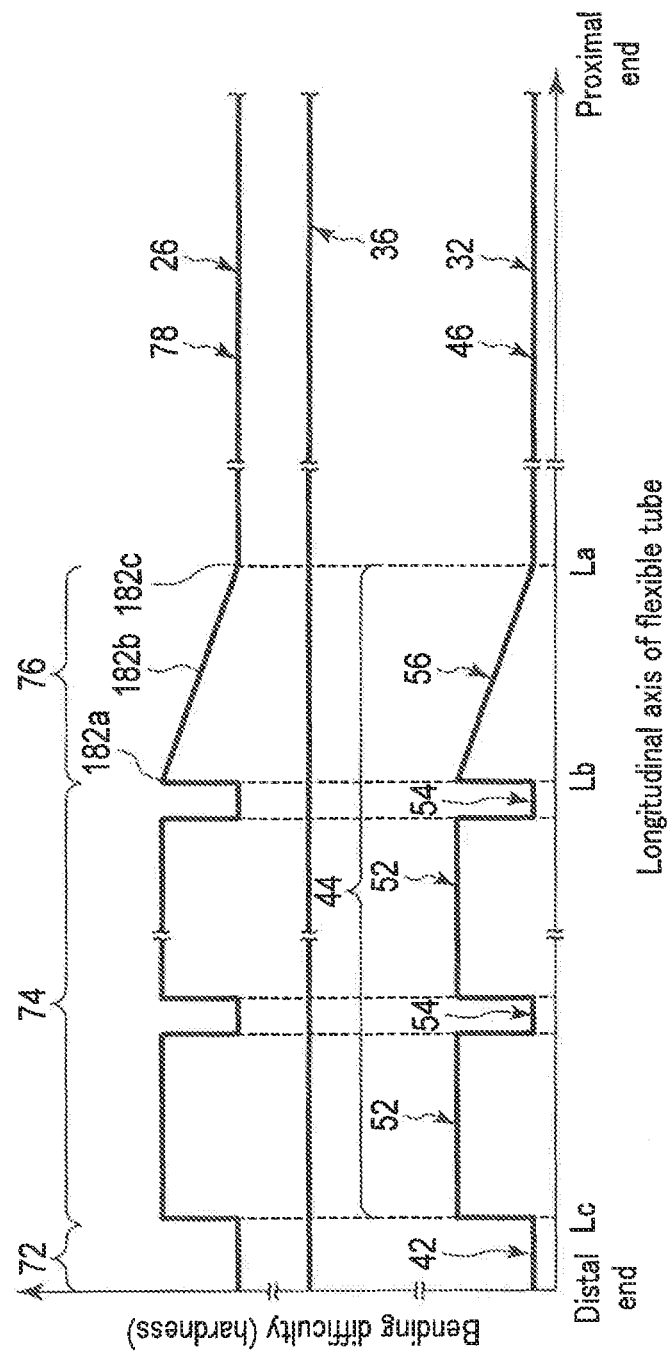
F I G. 5A

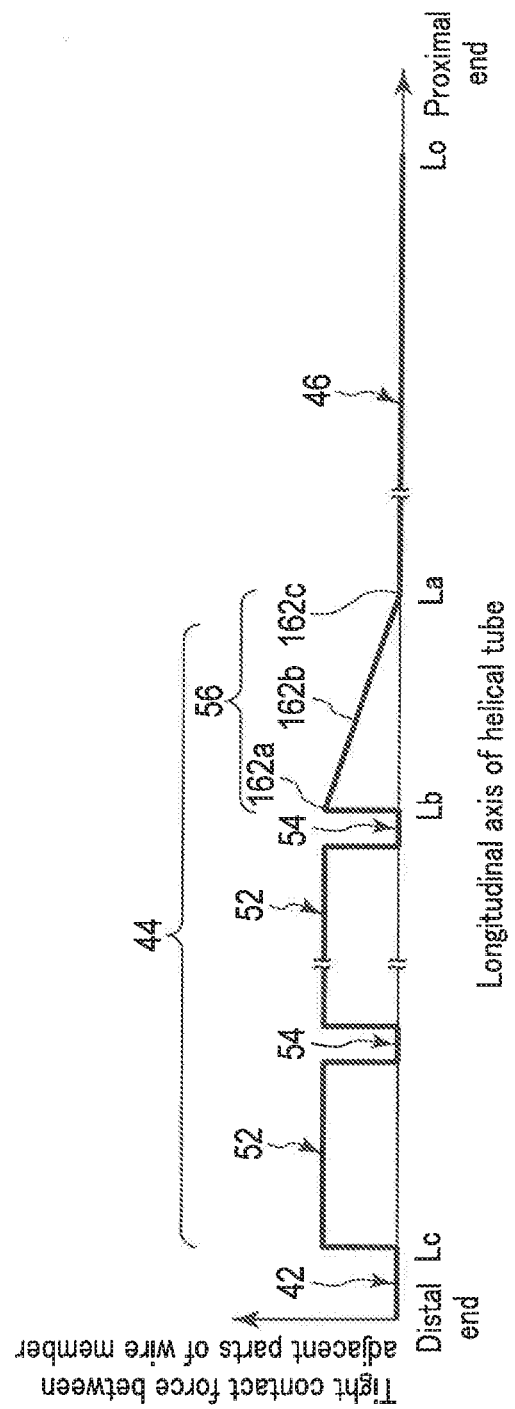
F I G. 5B

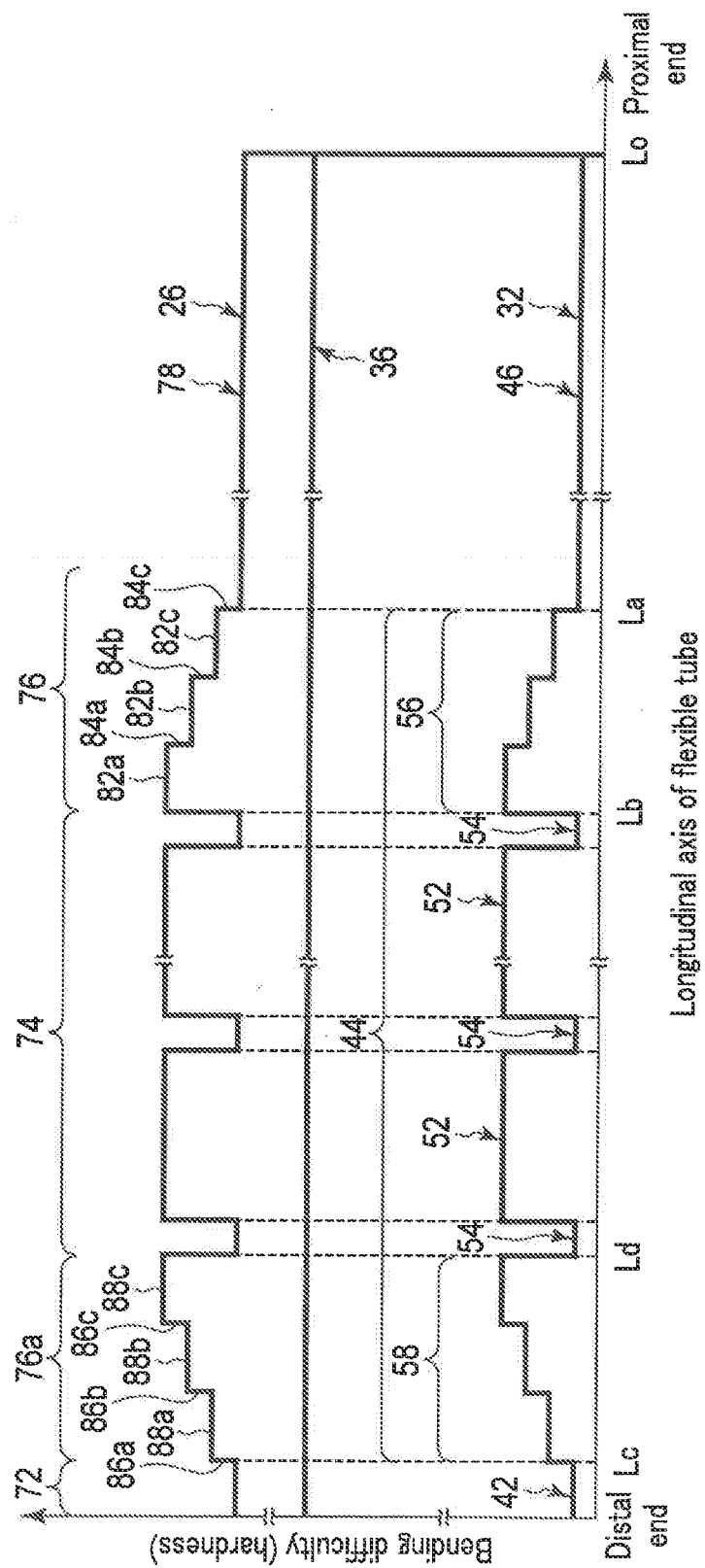
F I G. 10B

FLEXIBLE TUBE AND INSERTION APPARATUS

CROSS-REFERENCE TO RELATED APPLICATIONS

This application is a Continuation Application of PCT Application No. PCT/JP2015/083801, filed Dec. 1, 2015 and based upon and claiming the benefit of priority from prior Japanese Patent Application No. 2014-244360, filed Dec. 2, 2014, the entire contents of all of which are incorporated herein by reference.

BACKGROUND OF THE INVENTION

1. Field of the Invention

The present invention relates to a flexible tube used for an insertion section of an insertion apparatus of an endoscope, etc. which, for example, is inserted into a hole of a passage, etc., and an insertion apparatus including the flexible tube.

2. Description of the Related Art

Jpn. Pat. Appln. KOKAI Publication No. 2013-097327, for example, discloses a flexible tube that includes a helical tube, and an outer tube covered on an outer side of the helical tube. The helical tube includes a closely-wound region including a closely-wound portion having a tight contact force applied on adjacent parts of a wire member adjacent to each other along a longitudinal axis and a sparsely-wound portion where the adjacent parts of the wire member adjacent to each other are separated from each other along the longitudinal axis. The closely-wound portion and the sparsely-wound portion are arranged alternately along the longitudinal axis.

BRIEF SUMMARY OF THE INVENTION

According to one aspect of the present invention, a flexible tube which define a longitudinal axis by a distal end and a proximal end of the flexible tube, includes: a helical tube including: a closely-wound region including a closely-wound portion to which a tight contact force is applied, the tight contact force allowing adjacent parts of a wire member adjacent along the longitudinal axis to become a tight contact state, a sparsely-wound portion which is arranged at a proximal side of the closely-wound portion and where the adjacent parts of the wire member are arranged separately from each other along the longitudinal axis, and a change portion which is arranged at a proximal side of the sparsely-wound portion along the longitudinal axis and, while bringing the adjacent parts of the wire member in tight contact with each other along the longitudinal axis, has the tight contact force between the adjacent parts of the wire member on the proximal side rather than the distal side along the longitudinal axis reduced more than the tight contact force of the closely-wound portion; and a sparsely-wound region which is arranged continuously on a proximal side of the change portion along the longitudinal axis, wherein the adjacent parts of the wire member adjacent along the longitudinal axis are separated from each other; and a cylindrical outer tube which covers an outer side of the helical tube across its entire length, and defines the length of the helical tube.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4A is a schematic graph showing bending difficulties at positions along a longitudinal axis of the flexible tube, a helical tube, and an outer tube of the insertion section of the insertion apparatus according to the first embodiment.

FIG. 5A is a schematic graph showing bending difficulties at positions along the longitudinal axis of the flexible tube, the helical tube, and the outer tube of the insertion section of the insertion apparatus according to a first modification of the first embodiment.

FIG. 5B is a schematic graph showing a tight contact force between the adjacent parts of the wire member at positions along the longitudinal axis of the helical tube of the flexible tube of the insertion section of the insertion apparatus according to the first modification of the first embodiment.

FIG. 10B is a schematic graph showing bending difficulties at positions along a longitudinal axis of the flexible tube, a helical tube, and an outer tube of the insertion section of the insertion apparatus according to the second embodiment.

DETAILED DESCRIPTION OF THE INVENTION

Hereinafter, embodiments for implementing the present invention will be explained with reference to the drawings.

The first embodiment will be explained using FIG. 1 to FIG. 4B.

An insertion apparatus 10 according to the present embodiment will be explained assuming that it is, for example, a medical endoscope. The insertion apparatus 10 is not only preferred as being a medical endoscope, but also as being an industrial endoscope, or an insertion instrument such as a catheter which does not have an illumination optical system or an observation optical system.

Figure 1:
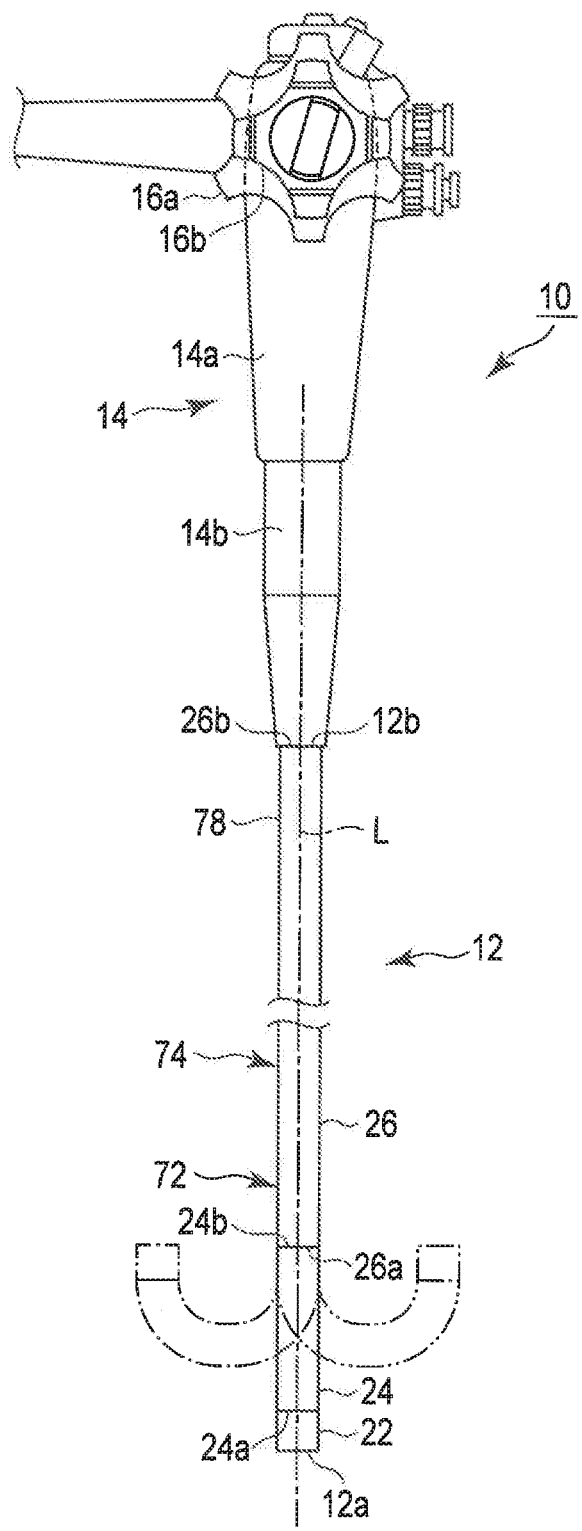
FIG. 1 is a schematic view of an endoscope as an insertion apparatus according to first and second embodiments.

As shown in FIG. 1, the insertion apparatus 10 according to the present embodiment includes: an insertion section 12 having a distal portion 12a and a proximal portion 12b; and a grip section (operation section) 14 located at the proximal portion 12b of the insertion section 12. The grip section 14 includes a grip section main body 14a gripped by a user and a protection hood 14b. The proximal portion 12b of the insertion section 12 is coupled to the grip section 14 through the protection hood 14b; which prevents the insertion section 12 from being bent, such as buckled, at the proximal portion 12b thereof.

Figure 3:
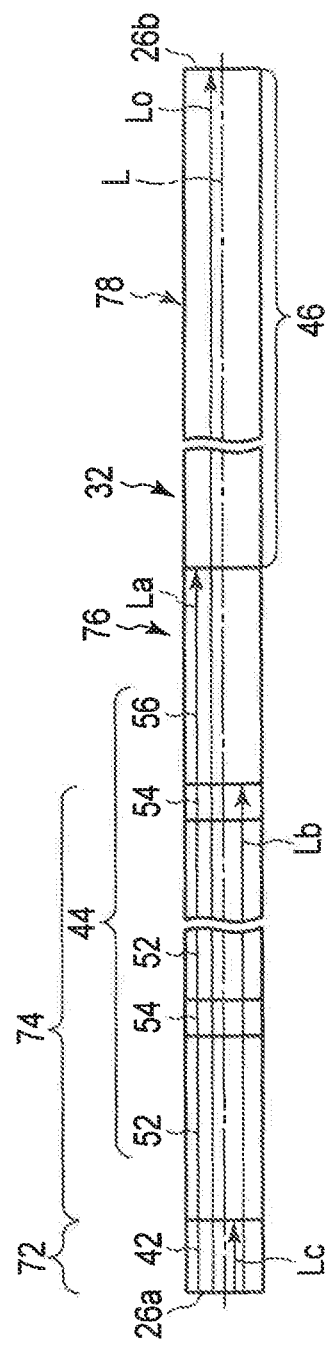
FIG. 3 is a schematic view showing the flexible tube of the insertion section of the insertion apparatus according to the first embodiment.

The distal portion 12a and proximal portion 12b of the insertion section 12 or the distal end 26a and proximal end 26b of a flexible tube 26 mentioned below define a longitudinal axis L as a central axis. As shown in FIG. 3, the length between the distal end 26a and the proximal end 26b of the flexible tube 26 is referred to as Lo.

As shown in FIG. 1, the insertion section 12 includes, from its distal end towards its proximal end, a distal rigid portion 22, a bending portion 24, and a flexible tube 26. The distal end 24a of the bending portion 24 is coupled to the distal rigid portion 22. The distal end 26a of the flexible tube 26 is coupled to the proximal end 24b of the bending portion 24. The proximal end 26b of the flexible tube 26 is coupled to the protection hood 14b of the grip section 14.

The bending portion 24 can be bent, for example, in four directions by operating the knobs 16a and 16b provided on the grip section main body 14a.

Figure 2:
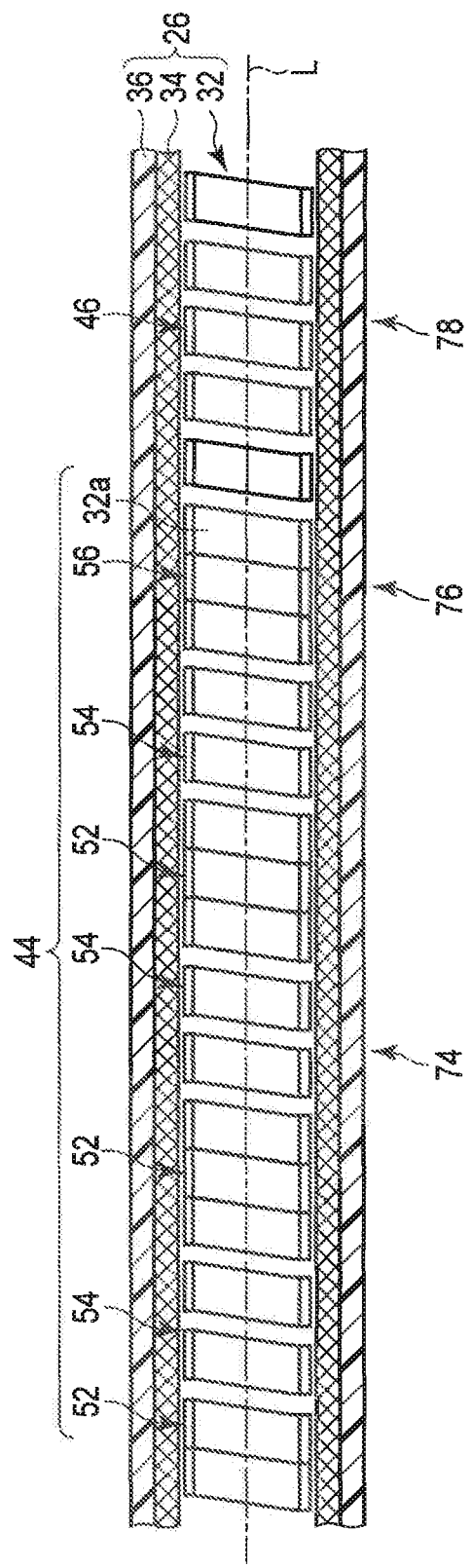
FIG. 2 is a schematic longitudinal sectional view of a flexible tube of an insertion section of the insertion apparatus according to the first and second embodiments.

As shown in FIG. 2, the flexible tube 26 includes a helical tube 32, a cylindrical and net-like braid 34, and a cylindrical outer tube 36 in a radial direction with respect to the central axis (longitudinal axis) L, from the inner side to the outer side thereof. The braid 34 is not indispensable. It is also preferable to have the outer side of the helical tube 32 covered directly by the outer tube 36.

The helical tube 32 is formed by winding a wire member 32a, Which is made of, for example, a metal such as stainless steel, and is an elongated band, around the longitudinal axis L. It is desirable that the helical tube 32 is formed to have a constant or substantially constant outer diameter and inner diameter from its distal end to its proximal end. The helical tube 32 is a spiral tubular member that is difficult to bend in a bending direction departing from the longitudinal axis L (for example, a direction perpendicular to the longitudinal axis L), and has resiliency tending to return to its original state from a bent state.

As shown in FIG. 2 and FIG. 3, the helical tube 32 of the flexible tube 26 is arranged on the longitudinal axis L and, from the distal end towards the proximal end along the longitudinal axis, includes a first sparsely-wound region (a region with normal resiliency which has lower resiliency than a region with high resiliency) 42, a closely-wound region (a region with high resiliency) 44, and a second sparsely-wound region (a region with normal resiliency which has lower resiliency than a region with high resiliency) 46 coupled to the proximal side of the closely-wound region 44. The first sparsely-wound region 42 is shorter than the closely-wound region 44, along the longitudinal axis L. The first sparsely-wound region 42 is shorter than the second sparsely-wound region (a region with normal resiliency which has lower resiliency than a region with high resiliency) 46, along the longitudinal axis L. The closely-wound region 44 is arranged continuously at the proximal side of the first sparsely-wound region 42, and is formed to have higher resiliency than the first sparsely-wound region 42. The second sparsely-wound region 46 is arranged continuously at the proximal side of the closely-wound region 44, and is formed to be bent easier than the closely-wound region 44 (see FIG. 4A)

When, for example, the insertion section 12 is inserted into a deep part of the large intestine from the anus, it is preferable that the length of the closely wound region 44 along the longitudinal axis L is formed about the same as or longer than the length when the large intestine is made essentially linear.

Figure 10A:
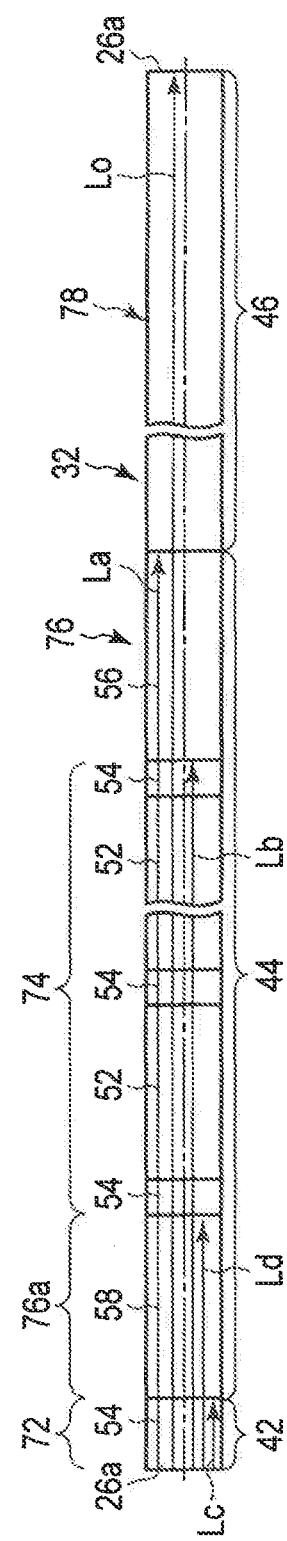
FIG. 10A is a schematic view showing a flexible tube of an insertion section of an insertion apparatus according to the second embodiment.

In the case where the insertion apparatus 10 is an endoscope used for the large intestine, the length (distance) Lb between the distal end 26a of the flexible tube 26 and the proximal end of a second flexible portion 74 is desirably 700 mm or so, and the length (distance) Lc between the distal end 26a of the flexible tube 26 and the distal end of the second flexible portion 74 is desirably 300 mm or so (see FIG. 3 and FIG. 10A). It is desirable that a third flexible portion 76 mentioned below is, for example, a few centimeters to ten centimeters or so. The above requirements are also applicable to each modification and the second embodiment mentioned below.

The length of the closely-wound region 44 along the longitudinal axis L, that is, a distance (length) La (<Lo) between the distal end 26a of the flexible tube 26 and the proximal end of the closely-wound region 44 (distal end of the second sparsely-wound region 46), is set as appropriate in accordance with a body portion to be examined. The length of the second sparsely-wound region 46 along the longitudinal axis L can also be set as appropriate.

The closely-wound region 44 includes a plurality of closely-wound portions 52 and a plurality of sparsely-wound portions 54 which are consecutively and alternately arranged along the longitudinal axis L. In other words, each sparsely-wound portion 54 is located between a plurality of closely-wound portions 52. In the case where the closely-wound portions 52 are three in number, the sparsely-wound portions 54 are at least two in number. That is, it is also preferable that there are two or more sparsely-wound portions 54.

It is desirable to have each closely-wound portion 52 formed longer than each sparsely-wound portion 54 along the longitudinal axis L in the closely-wound region 44. In the present embodiment, in the closely-wound region 44, it is desirable to have the sum of the lengths of the closely-wound portions 52 along the longitudinal axis L larger than the sum of the lengths of the sparsely-wound portions 54 along the longitudinal axis L. It is desirable to have the length of at least one of the plurality of closely wound portions 52 along the longitudinal axis L longer than the length of a change portion 56 of a tight contact force (mentioned below) along the longitudinal axis L.

Figure 4B:
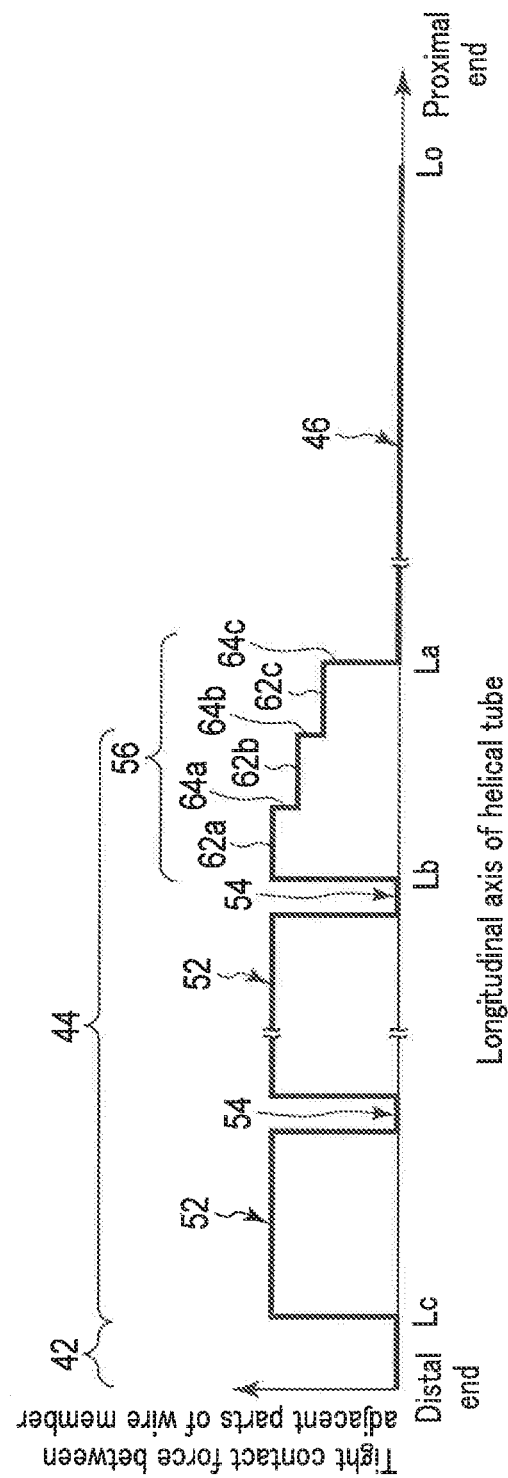
FIG. 4B is a schematic graph showing a tight contact force between adjacent parts of a wire member at positions along the longitudinal axis of the helical tube of the flexible tube of the insertion section of the insertion apparatus according to the first embodiment.

As shown in FIG. 2 and FIG. 4B, a tight contact force (≤initial tension) is applied to each closely-wound portion 52, thus enabling the adjacent parts of the wire member 32*a* adjacent with each other along the longitudinal axis L to come into a tight contact state with each other by the initial tension that brings the adjacent parts of the wire member 32*a* adjacent along the longitudinal axis L in a tight contact state. The initial tension (tight contact force) to be applied here can be adjusted as appropriate, for example, by how the wire member 32*a* is wound. Here, it is assumed that the tight contact force that is based on the initial tension between the adjacent parts of the wire member 32*a* in the closely-wound portions 52 is essentially constant at any position.

The tight contact force of the adjacent parts of the wire member 32*a* can be changed by changing the structure of the winding, or the width and plate thickness of the adjacent parts of the wire member 32*a* itself, etc. as appropriate.

When the longitudinal axis L of the closely-wound portion 52 is arranged vertically, the tight contact force maintains a state where the adjacent parts of the wire member 32*a* of the closely-wound portion 52 are in tight contact against the force of gravity, and no gap is provided between the adjacent parts of the wire member 32*a*. If an external force is applied against the longitudinal axis L of the closely-wound portion 52 in a state where the longitudinal axis L is arranged, for example, horizontally, a gap between the adjacent parts of the wire member 32*a* is extremely unlikely to be formed until the external force reaches a force that cancels out the tight contact force. In this manner, the closely-wound portion 52 is prevented from deflecting. If the external force applied against the longitudinal axis L exceeds the tight contact force between the adjacent parts of the wire member 32*a*, a gap will be produced between the tightly contacted adjacent parts of the wire member 32*a* of the closely-wound portion 52. As a result, the closely-wound portion 52 will be deflected. Therefore, due to the tight contact force applied to the adjacent parts of the wire member 32*a* adjacent along the longitudinal axis L, the closely-wound portion 52 has a large bending rigidity before the closely-wound portion 52 begins to bend. After the closely-wound portion 52 begins to bend and is deprived of the tight contact force, it bends in accordance with the spring constant of the helical tube 32. That is, as shown in FIG. 4A and FIG. 4B, the magnitude of the tight contact force applied to the adjacent parts of the wire member 32*a* corresponds to the difficulty of bending the helical tube 32. Therefore, when inserting the insertion section 12 into an appropriate passage, once the closely-wound portion 52 of the flexible tube 26 starts bending, the flexible tube 26 can be bent as if the closely-wound portion 52 does not exist.

In the state where the closely-wound portion 52 is bent, the tight contact force between the adjacent parts of the wire member 32*a* along the longitudinal axis L of the closely-wound portion 52 helps exhibit the resiliency that enables the closely-wound portion 52 to return to its original state. That. is, the magnitude of the tight contact force applied to the adjacent parts of the wire member 32*a* corresponds to the resiliency of the helical tube 32. In particular, in the case where the gaps between the adjacent parts of the wire member 32*a* of the closely-wound portion 52 are narrow (in the case where the radius of curvature of the closely-wound portion 52 is large in the bent state), the closely-wound portion 52 exhibits a higher resiliency than each sparsely-wound portion 54.

As shown in FIG. 2, in each sparsely-wound portion 54, the adjacent parts of the wire member 32*a* adjacent in a direction along the longitudinal axis L are separated from each other by given intervals (pitches). In the sparsely-wound portion 54, the adjacent parts of the wire member 32*a* are separated from each other, and a tight contact force is not applied between the adjacent parts of the wire member 32*a* (see FIG. 4B). Therefore, as shown in FIG. 4A, the sparsely-wound portion 54 is formed easier to bend in a direction departing from the longitudinal direction L (for example, a perpendicular direction) than the closely-wound portion 52. I the sparsely-wound portion 54, the intervals at which the adjacent parts of the wire member 32*a* are arranged need not be constant; the intervals may be shortened or lengthened, depending upon the portions. The sparsely-wound portion 54 is formed easier to bend in the longitudinal axis L than not only the closely-wound portion 52, but also the adjuster 56 with the tight contact force mentioned below.

Each sparsely-wound portion 54 has spring characteristics Therefore, each sparsely-wound portion 54 exhibits appropriate resiliency by which each sparsely-wound portion 54 attempts to return to the original state from the bent state. However, unlike the adjacent parts of the wire member 32*a* of the closely-wound portion 52, a tight contact force is not applied to the adjacent parts of the wire member 32*a* of each sparsely-wound portion 54. Therefore, the resiliency of each sparsely-wound portion 54 is lower than that of the closely-wound portion 52.

As shown in FIG. 2 to FIG. 4B, the closely-wound region 44 includes, at a position on the proximal end thereof, the change portion 56 in which the tight contact force between the closely-wound adjacent parts of the wire member 32*a* is changed from that of the closely-wound portion 52. The distal end of the change portion 56 (a position from the distal end 26*a* of the flexible tube 26 to distance Lb) is arranged continuously at the proximal end of the sparsely-wound portion 54 positioned at the most proximal end. The proximal end of the change portion 56 (a position from the distal end 26*a* of the flexible tube 26 to distance La) is arranged continuously at the distal end of the second sparsely-wound region 46. The entire length of the change portion 56 is defined by La-Lb.

The helical tube 32 may be obtained by integrally forming the closely-wound portion 52, the sparsely-wound portion 54, the change portion 56 of the closely-wound region 44, and also the second sparsely-wound region 46 by one wire member 32a. Alternatively, each wire member 32a of a first helical tube integrally forming the closely-wound portion 52 and the sparsely-wound portion 54, a second helical tube forming the change portion 56 of the closely-wound region 44, and a third helical tube forming the second sparsely-wound region 46 may be joined by welding, for example, to form one helical tube 32.

The change portion 56 is formed by an tension being applied that brings the adjacent parts of the wire member 32a adjacent in a direction along the longitudinal axis L together in a tight contact state. Therefore, a tight contact force that brings the adjacent parts of the wire member 32a adjacent in a direction along the longitudinal axis L together in a tight contact state is applied to the change portion 56.

As shown in FIG. 4B, in the present embodiment, the tight contact force between the adjacent parts of the wire member 32a in the change portion 56 is made to decrease gradually along the longitudinal axis L from the distal side towards the proximal side. Specifically, the varying portion 56 includes from the distal side towards the proximal side thereof a first portion 62a which maintains the tight contact force between the adjacent parts of the wire member 32a the same as the closely-wound portion 52 in a constant manner, a second portion 62b which maintains the contact force between the adjacent parts of the wire member 32a constant in a state where it is made lower than the first portion 62a, and a third portion 62c which maintains the tight contact force between the adjacent parts of the wire member 32a constant in a state where is made lower than the second portion 62b. The change portion 56 includes a first reduction portion 64a between the first portion 62a and the second portion 62b. The first reduction portion 64a reduces the tight contact force of the first portion 62a to the tight contact force of the second portion 62b. The change portion 56 includes a second reduction portion 64b between the second portion 62b and the third portion 62c. The second reduction portion 64b reduces the tight contact force of the second portion 62b to the tight contact force of the third portion 62c. The change portion 56 includes a third reduction portion 64c between the third portion 62c and the second sparsely-wound region 46. The third reduction portion 64c reduces the tight contact force of the third portion 62c to the tight contact force of the second sparsely-wound region 46. As will be explained below, in the second sparsely-wound region 46, since the adjacent parts of the wire member 32a are located apart from each other, the tight contact force is zero.

In the present embodiment, the lengths of each of the first reduction portion 64a, the second reduction portion 64b, and the third reduction portion 64c along the longitudinal axis L is preferably within a few millimeters. Since the first reduction portion 64a, the second reduction portion 64b, and the third reduction portion 64c are shorter than the other portions, they are described by a vertical line in FIG. 4B. In this manner, in the first reduction portion 64a, the second reduction portion 64b, and the third reduction portion 64c, the tight contact force is reduced in a small range from the distal end towards the proximal end thereof. However, the amount of reduction of each of the first reduction portion 64a, the second reduction portion 64b, and the third reduction portion 64c is smaller than the amount of reduction between the closely-wound portion 52 and the sparsely-wound portion 54.

The length of the first portion 62a, the second portion 62b, the third portion 62c, and the change portion 56, and the relative length of the first portion 62a, the second portion 62b, and the third portion 62c, are not particularly limited. The magnitude (reduction range) of the first reduction portion 64a, the second reduction portion 64b, and the third reduction portion 64c is not particularly limited. The number of these portions and reduction portions are not particularly limited.

In the above manner, in the change portion 56 of the helical tube 32, the tight contact force is reduced in stages from its distal side towards its proximal side so as to be approximated to the tight contact force of the second sparsely-wound region 46 (a state in which the tight contact force is zero) from a state of having the same tight contact force as the closely-wound portion 52.

The first sparsely wound region 42 and the second sparsely-wound region 46 are preferred to be formed in the same manner as the sparsely-wound portion 54 of the closely-wound region 44. That is, in the first sparsely-wound region 42 and the second sparsely-wound region 46, the adjacent parts of the wire member 32a adjacent in a direction along the longitudinal axis L are separated from each other by a given distance. In the first sparsely-wound region 42 and the second sparsely-wound region 46, the adjacent parts of the wire member 32a are separated from each other, and a tight contact force is not applied between the adjacent parts of the wire member 32a (see FIG. 4B). Therefore, the first sparsely-wound region 42 and the second sparsely-wound region 46 can be bent more easily than the closely-wound portion 52 and the change portion 56, in the same manner as the sparsely-wound portion 54. When an external force is applied thereto in a direction departing from the longitudinal axis L (for example, a direction perpendicular to the longitudinal axis L), they are bent more easily in comparison to when an external force is applied to the closely wound region 44, with a lower resiliency than the closely-wound region 44.

The outer tube 36 is made of an appropriate resin material that suppresses extension and contraction in the direction of the longitudinal axis L, and is formed, for example, by extrusion molding. The bending difficulty and resiliency of the outer tube 36 can be set as appropriate. The resin material forming the outer tube 36 is preferably heat- and chemical-resistant and formed of a material that can be repeatedly cleaned and sterilized. The resin material is also preferably electrically insulative (non-conductive).

The outer tube 36 covers the outer side of the helical tube 32 across its entire length. The outer tube 36 defines the length of the flexible tube 26. It is assumed here that the bending difficulty and resiliency of the outer tube 36 are constant from its distal end to its proximal end.

The outer tube 36 defines the overall length Lo of the flexible tube 26, and suppresses the overall length Lo of the helical tube 32 from changing. When assuming that the overall length of the helical tube 32 does not change and applying an external force to the closely-wound region 44 from a direction departing from the longitudinal axis L (for example, a direction perpendicular to the longitudinal axis L), the closely-wound region 44 is bent with the sparsely-wound portion 54 mainly serving as a buffer. That is, the closely-wound portion 52 can be bent at an appropriate position by narrowing the gaps between the adjacent parts of the wire member 32a of the sparsely-wound portion 54.

When the closely-wound region 44 is bent while the overall length Lo of the flexible tube 26 is maintained by the outer tube 36, the sparsely-wound portion 54 absorbs the extension of the flexible tube 32 in the direction along the longitudinal axis L, which is caused by the extension of the closely-wound portion 52 in the direction along the longitudinal axis L in the axial direction of the flexible tube 32. Therefore, the sparsely-wound portion 54 of the closely-wound region 44 cancels the extension of the flexible tube 32 in the direction along the longitudinal axis L. Therefore, the presence of the sparsely-wound portion 54 in addition to the closely-wound portion 52 allows the closely-wound region 44 to be bent smoothly in a state where the characteristics of the closely-wound portion 52 with high spring characteristics against the sparsely-wound portion 54 is maintained. Furthermore, the resiliency based on the tight contact force of the closely-wound portion 52 allows the closely-wound region 44 to return to an approximately straight state from the bent state while the overall length is maintained by the outer tube 36.

Not only when the external force is applied to the closely-wound portion 52 of the closely-wound region 44, but also when it is applied to the sparsely-wound portion 54, the closely-wound region 44 can be bent while the sparsely-wound portion 54 receiving the external force and the other sparsely-wound portions 54 function as a buffer. Likewise the sparsely-wound portion 54 of the closely-wound region 44, the first and second sparsely-wound regions 42 and 46 can also function as a buffer.

The first sparsely-wound region 42 of the helical tube 32 and the outer tube 36 on the outer side of the first sparsely-wound region 42 cooperate with each other to form a first flexible portion 72. The closely-wound portion 52 and the sparsely-wound portion 54 of the closely-wound region 44 of the helical tube 32 and the outer tube 36 on the outer side of the closely-wound region 44 cooperate with each other to form a second flexible portion 74. The change portion 56 of the closely-wound region 44 of the helical tube 32 and the outer tube 36 on the outer side of the closely-wound region 44 cooperate with each other to form a third flexible portion 76. The second sparsely-wound region 46 of the helical tube 32 and the outer tube 36 on the outer side of the second sparsely-wound region 46 cooperate with each other to form a fourth flexible portion 78.

Here, as shown in FIG. 4A, generally, the bending difficulty of the first flexible portion 72 can be regarded as the sum of the bending difficulty of the first sparsely-wound region 42 and the outer tube 36 arranged radially outward in sequence from the longitudinal axis L. The resiliency of the first flexible portion 72 can generally be regarded as the sum of the resiliency of the first sparsely-wound region 42 and the outer tube 36 arranged radially outward in sequence from the longitudinal axis L. Each of the bending difficulty and resiliency of the first flexible portion 72 is essentially constant.

The bending difficulty of the second flexible portion 74 can generally be regarded as the sum of the bending difficulty of the closely-wound portion 52 of the closely-wound region 44 of the helical tube 32 and the outer tube 36, or the sum of the bending difficulty of the sparsely-wound portion 54 and the outer tube 36 arranged radially outward in sequence from the longitudinal axis L. That is, the bending difficulty of the second flexible portion 74 can be regarded as the sum of the bending difficulty of the closely-wound region 44 and the outer tube 36. The resiliency of the second flexible portion 74 can generally be regarded as the sum of the resiliency of the closely wound portion 52 of the closely-wound region 44 of the helical tube 32 and the outer tube 36, or the sum of the resiliency of the sparsely-wound portion 54 and the outer tube 36 arranged radially outward in sequence from the longitudinal axis L. That is, the resiliency of the second flexible portion 74 can be regarded as the sum of the resiliency of the closely-wound region 44 and the outer tube 36. From a microscopic point of view, the bending difficulty and resiliency of the second flexible portion 74 change depending upon whether the position includes the closely-wound portion 52 or the portion includes the sparsely-wound portions 54. From a macroscopic point of view, that is, when considering the entirety of the second flexible portion 74 where the outer tube 36 covers the closely-wound region 44, the bending difficulty and the resiliency are respectively essentially constant. When using the flexible tube 26, the user of the insertion apparatus 10 may consider the latter as being the case. This is attributable to the fact that the sparsely-wound portion 54 is shorter than the closely-wound portion 52.

The bending difficulty of the third flexible portion 76 can generally be regarded as the sum of the bending difficulty of the change portion 56 of the helical tube 32 and the outer tube 36 arranged radially outward in sequence from the longitudinal axis L. The resiliency of the third flexible portion 76 can generally be regarded as the sum of the resiliency of the change portion 56 of the helical tube 32 and the outer tube 36 arranged radially outward in sequence from the longitudinal axis L.

That is, the third flexible portion 76 includes from the distal side towards the proximal side thereof a first portion 82a that has the same bending difficulty as the bending difficulty of where the closely-wound portion 52 is covered with the outer tube 36, a second portion 82b that is bent easier and has a lower resiliency than the first portion 82a and maintains an appropriate bending difficulty and resiliency, and a third portion 82c that is bent easier and has a lower resiliency than the second portion 82b and maintains an appropriate bending difficulty and resiliency. The third flexible portion 76 includes a first reduction portion 84a located between the first portion 82a and the second portion 82b. The first reduction portion 84a reduces the bending hardness and resiliency of the first portion 82a to those of the second portion 82b. The third flexible portion 76 includes a second reduction portion 84b located between the second portion 82b and the third portion 82c. The second reduction portion 84b reduces the bending difficulty and resiliency of the second portion 82b to those of the third portion 82c. The third flexible portion 76 includes a third reduction portion 84c located between the third portion 82c and the fourth flexible portion 78. The third reduction portion 84c reduces the bending difficulty and resiliency of the third portion 82c to those of the fourth flexible portion 78.

Here, refer to FIG. 4B, in addition to FIG. 4A. From a microscopic point of view, the bending difficulty and resiliency of the third flexible portion 76 change depending upon whether the position includes the first portion 62a (first portion 82a), the second portion 62b (second portion 82b), or the third portion 62c (third portion 82c). With this structure, the bending difficulty and resiliency of the third flexible portion 76 decrease stepwise from the distal end to the proximal end. From a macroscopic point of view, that is, when considering the entirety of the third flexible portion 76 where the outer tube 36 covers the change portion 56, the bending difficulty and resiliency of the third flexible portion 76 decrease essentially linearly from the distal end to the proximal end. When using the flexible tube 26, the user of the insertion apparatus 10 may consider the latter as being the case. This is because the third flexible portion 76 itself is formed comparatively shorter than the second flexible portion 74 and the fourth flexible portion 78, and the first to third reduction portions 64a, 64b, and 64c are shorter than the first to third portions 62a, 62b, and 62c, and, furthermore, the amount of reduction of each reduction portion 64a, 64b, and 64c is small.

The bending difficulty of the fourth flexible portion 78 can generally be regarded as the sum of the bending difficulty of the second sparsely-wound region 46 of the helical tube 32 and the outer tube 36 arranged radially outward in sequence from the longitudinal axis L. The resiliency of the fourth flexible portion 78 can generally be regarded as the sum of the resiliency of the second sparsely-wound region 45 of the helical tube 32 and the outer tube 36 arranged radially outward in sequence from the longitudinal axis L. The bending difficulty and resiliency of the fourth flexible portion 78 are essentially constant.

The first flexible portion 72 and the fourth flexible portion 78 are formed to be bent comparatively easily. The first flexible portion 72 is easier to bend than the second flexible portion 74. The third flexible portion 76 is easier to bend than the second flexible portion 74, and is more difficult to bend than the fourth flexible portion 78. That is, the third flexible portion 76 is formed between the second flexible portion 74 and the fourth flexible portion 78 with a bending difficulty/easiness corresponding to those between the second and fourth flexible portions 74 and 78. The bending difficulty/bending easiness of the third flexible portion 76 is gradually approximated from the second flexible portion 74 to the fourth flexible portion 78 as it transitions from its distal side towards its proximal side along the longitudinal axis L. In the third flexible portion 76, the resiliency is gradually approximated from the second flexible portion 74 to the fourth flexible portion 78 as it transitions from its distal side towards its proximal side along the longitudinal direction L.

In the following, the operation of the insertion apparatus 10 of the present embodiment will be explained.

The user of the insertion apparatus 10 grips the grip section 14 and, for example, the second flexible portion 74 and/or the third flexible portion 76 of the flexible tube 26. Then, the user inserts the insertion section 12 in the order of the distal rigid portion 22, the bending portion 24, and the flexible tube 26 into a hole of an appropriate narrow and curved passage, such as the large intestine. While operating the knobs 16a and 16b to appropriately bend the bending portion 24, the user changes the holding position of the flexible tube 26 gradually toward the proximal side, thereby allowing the insertion section 12 to be inserted further into the passage.

The first flexible portion 72 is bent easier than the second flexible portion 74. The second flexible portion 74 is more difficult to bend than the first flexible portion 72; however, the bending difficulty of the second flexible portion 74 is such that, it can be bent by an external force received from the inner circumferential surface (inner wall) of the curved portion of passage of the large intestine.

When the insertion section 12 is inserted from an opening (for example, the anus) of a flexible passage, such as the large intestine, further into the passage (deep part of the large intestine), an external force (including a force of gravity) is applied from the inner circumferential surface (inner wall) of the passage to the first and second flexible portions 72 and 74 from a direction departing from the direction along the longitudinal axis L (for example, a perpendicular direction) of the flexible tube 26. In the case where the applied external force is smaller than the bending difficulty of the first flexible portion 72, the first flexible portion 72 is not deflected and maintains a linear state. Likewise, in the case where the applied external force is smaller than the bending difficulty of the second flexible portion 74, the second flexible portion 74 is not deflected and is inserted into the passage while maintaining the linear state.

If the external force (including the force of gravity) applied from the inner circumferential surface of the passage exceeds the bending difficulty of the first flexible portion 72, the first flexible portion 72 begins to deflect from the essentially linear state. That is, the first flexible portion is bent from the essentially linear state.

In the case of inserting the distal portion 12a of the insertion section 12 into the passage from, for example, the anus to a deep part of the large intestine, the first flexible portion 72 can be bent appropriately along the inner circumferential surface of the passage. The second flexible portion 74 is also bent by the application of an external force exceeding the bending difficulty received from the inner circumferential surface of the passage. Thus, the insertion section 12, including the first flexible portion 72 and the second flexible portion 74, bends along the curve of the flexible passage such as the large intestine.

The second flexible portion 74 has a higher resiliency than the first flexible portion 72. The resiliency of the second flexible portion 74 allows the second flexible portion 74 to be easily returned to the approximately straight state from the bent state. Therefore, after the first flexible portion 72 passes a curve of the passage, the second flexible portion 74 utilize its resiliency to make the curved portion of the passage essentially linear. After the second flexible portion 74 is bent, the insertion section 12 is pulled a little so that the external force applied to the second flexible portion 74 is reduced. This allows the second flexible portion 74 to exhibit its resiliency more easily. Because of this, a passage having a small bending radius, such as the sigmoid colon, can be made essentially linear. Since the first flexible portion 72 is also resilient, it returns to an approximately straight state. Therefore, the essentially-linear flexible tube 26 can easily pass through the essentially-linear passage. In this manner, the distal end 12a of the insertion section 12 can be inserted into a deep part of the passage.

After the first flexible portion 72 and the second flexible portion 74 are appropriately bent in sequence and pass the curve of the passage, the passage is made essentially linear by the resiliency of the second flexible portion 74. By doing so, a so-called sticking phenomenon can be prevented, in which the distal portion 12a of the insertion section 12 or the distal end 26a of the flexible tube 26 pushes the inner wall of the large intestine.

In this manner, the first and second flexible portions 72 and 74 of the flexible tube 26 of the insertion section 12 are appropriately bent in response to the external force applied from the inner circumferential surface of the passage, and, while making the passage essentially linear by the resiliency of the second flexible portion 74, the distal end 12a of the insertion section 12 is made to move further into the passage.

Let us assume that the distal portion 12a of the insertion section 12 is inserted further into the passage, and the proximal end of the second flexible portion 74 of the flexible tube 26 (a position of length Lb from the distal end 26a of the flexible tube 26 (see FIG. 3 to FIG. 4B)) stops short of entering (outside the body) the opening (the anus) of the passage. In particular, let us assume that the proximal end of the second flexible portion 74 is in the vicinity of the opening (the anus) of the passage. If an affected portion is at a position further into the passage, the user holds the third flexible portion 76 and/or the fourth flexible portion 78 to push the insertion section 12 into the passage, and moves the distal portion 12a of the insertion section 12 further into the passage. Here, the third flexible portion 76 makes the bending difficulty (hardness) of the flexible tube 26 change gradually at the boundary of the second flexible portion 74 and the third flexible portion 76, and the boundary of the third flexible portion 76 and the fourth flexible portion 78. That is, each of the first to third reduction portions 84a, 84b, and 84c of the third flexible portion 76 makes the difference (change) in the bending difficulty between the second flexible portion 74 and the fourth flexible portion 78 along the longitudinal axis L gradual. With this structure, a drastic difference in the bending difficulty along the longitudinal axis L in the case where the fourth flexible portion 78 is connected directly to the closely-wound portion 52 positioned on the most proximal end of the second flexible portion 74 may be suppressed from occurring.

Therefore, the portion from the proximal end position of the second flexible portion 74 of the flexible tube 26 to the proximal side of the flexible tube 26 is suppressed to the greatest extent possible from being deflected by buckling. Here, when the insertion section 12 is pushed further into the passage, the presence of the third flexible portion 76 allows the transmission of force, between the position of the third flexible portion 76 and/or the fourth flexible portion 78 held by the user and the proximal end portion of the second flexible portion 74, to be performed favorably in comparison to the case where the fourth flexible portion 78 is connected directly to the closely-wound portion 52 positioned at the most proximal end of the second flexible portion 74. That is, the force that the user applies when pushing the third flexible portion 76 and/or the fourth flexible portion 78 of the flexible tube 26 along the longitudinal axis L is reliably transmitted from its position to the distal end 26a of the first flexible portion through the third flexible portion 76 and the second flexible portion 74.

By arranging the third flexible portion 76 between the second flexible portion 74 and the fourth flexible portion 78, even if an advancing force is applied along the longitudinal axis L at any position from the proximal end position of the second flexible portion 74 to the proximal side of the flexible tube 26, deflecting (buckling) at such position can be suppressed. Therefore, the amount of operating force at the third flexible portion 76 and/or the fourth flexible portion 78 held by the user of the insertion apparatus 10 is easily transmitted from the held position to the distal end 26a of the flexible tube 26 (the distal end of the first flexible portion 72), allowing the flexible tube 26 to be easily inserted further into the passage. In other words, the distal end 12a of the insertion section 12 can be easily inserted further into the passage. In this manner, the third flexible portion 76 functions as a force transmission part and a deflecting suppression part.

As explained above, the insertion apparatus 10 according to the present embodiment may be considered as follows.

The flexible tube 26 of the present embodiment includes a helical tube 32 and an outer tube 36 that covers the outer side of this helical tube 32. The helical tube 32 includes a tight contact force change portion 56 between the sparsely-wound portion 54 at the most proximal side of the closely-wound region 44 and the second sparsely-wound region 46, and makes the tight contact force between the adjacent parts of the wire member 32a positioned closer to the proximal side than the distal side along the longitudinal axis L further reduced in comparison to the tight contact force of the closely-wound portion 52. That is, in the present embodiment, the change portion 56 is arranged at the proximal end position of the closely-wound region 44 of the helical tube 32 to form a third flexible portion 76 which gradually changes the bending difficulty between the second flexible portion 74 and the fourth flexible portion 78 from the bending difficulty of the second flexible portion 74 to the bending difficulty of the fourth flexible portion 78 from its distal side towards its proximal side.

Therefore, the third flexible portion 76 allows the change (difference) in the bending difficulty in the direction along the longitudinal axis L to be more gradual than when the fourth flexible portion 78 is arranged directly at the closely-wound portion 52 positioned at the most proximal end of the second flexible portion 74. When the user pushes the insertion section 12, that is, the flexible tube 26, further into the passage while holding the third flexible portion 76 and/or the fourth flexible portion 78, the force applied by the user can be reliably transmitted to the distal end 26a of the flexible tube 26. Therefore, when the user pushes the insertion section 12, that is, the flexible tube 26, further into the passage while holding the third flexible portion 76 and/or the fourth flexible portion 78, the third flexible portion 76 between the distal end of the fourth flexible portion 78 and the proximal end of the second flexible portion 74, and the distal end portion of the fourth flexible portion 78 itself can be prevented from being deflected (buckled).

Since the bending difficulty of the portion between the second flexible portion 74 and the fourth flexible portion 78 is adjusted by the third flexible portion 76 including the change portion 56 of the helical tube 32, the pushing force against the passage from the third and/or fourth flexible portions 76 and 78 of the flexible tube 26 towards the distal end 26a of the first flexible portion 72 can further be easily transmitted.

Furthermore, by arranging the second flexible portion 74 including the closely wound region 44 at the distal side of the flexible tube 26, favorable resiliency can be exhibited while exhibiting favorable bendability with respect to the external force against the passage. Therefore, the flexible tube 26 of the insertion section 12 bends in accordance with a curve of the flexible passage, such as the large intestine. After the second flexible portion 74 passes the curve of the passage, the resiliency (the property of the bent flexible tube 26 that tends to return to the linear state) of the flexible tube 26 is utilized to make the curve of the passage essentially linear, thereby allowing the flexible tube 26 to be inserted into a deep part of the passage. As described above, when being inserted, the flexible tube 26 of the present embodiment is capable of more easily making the passage essentially linear than a flexible tube with low resiliency.

Therefore, the present embodiment is capable of providing a flexible tube 26 that can be easily pushed further into a narrow hole such as a winding passage of, for example, the large intestine, from a partly inserted state, and an insertion apparatus 10 including such flexible tube 26.

Incidentally, the large intestine is a long organ having a number of curves. When the insertion section 12 of the insertion apparatus 10 is inserted into the large intestine, the flexible tube 26 needs to bend in accordance with the curves of the intestine. However, if the insertion section 12 is simply pushed and inserted in accordance with the curves, the large intestine may be excessively extended. In addition, a long time may be required for the insertion section 12 to pass through the large intestine with a number of curves and reach the appendix. If the large intestine is significantly extended, the insertion section 12 may not reach the appendix.

Therefore, as a technique for inserting the insertion section 12 into the large intestine, after the flexible tube 26 passes a curve of the large intestine, the resiliency of the flexible tube 26 (the property of the bent flexible tube 26 that tends to return to a linear state) is utilized to make the curve of the large intestine essentially linear. Accordingly, in order to facilitate the insertion of the insertion section 12 into the large intestine, it is effective to use a flexible tube 26 having high (strong) resiliency for making the large intestine essentially linear.

In the closely-wound region 44 of the flexible tube 26 of the present embodiment, an initial tension (tight contact force) is applied to the adjacent parts of the wire member 32a of the helical tube 32 along the longitudinal axis L. Therefore, resiliency can be enhanced, facilitating insertion of the flexible tube 26 into the large intestine.

The relation of the bending difficulties between the helical tube 32 and the outer tube 36 can be set as appropriate. That is, the outer tube 36 may be designed more difficult to bend (harder) than the helical tube 32, or the outer tube 36 may be designed easier to bend than the helical tube 32. As will be explained below, the bending difficulty of the outer tube 36 may be partially changed along the longitudinal axis L.

In the following, a first modification of the first embodiment will be described using FIG. 5A and FIG. 5B.

Here, a modification of the change portion 56 of the helical tube 32 will be explained. As shown in FIG. 5B, the distal end of the change portion 56 according to the present modification includes a first portion 162a having the same tight contact force as the closely-wound portion 52 between the adjacent parts of the wire member 32a. The change portion 56 of the present modification includes a second portion 162b whose tight contact force between the adjacent parts of the wire member 32a is reduced linearly from its distal end towards its proximal end. Here, the second portion 162b serves as a reduction portion that reduces the bending difficulty of the change portion 56 linearly. That is, the tight contact force between the adjacent parts of the wire member 32a of the change portion 56 is gradually reduced. The change portion 56 includes a third portion 162c having the same tight contact force as the second sparsely-wound region 46 (a state where the tight contact force is zero) at a position on the most proximal end of the change portion 56. That is, although the adjacent parts of the wire member 32a at the most proximal end of the change portion 56 contact each other, a tight contact force is not applied.

As shown in FIG. 5A, the third flexible portion 76 includes, from its distal side towards its proximal side, a first portion 182a which is as difficult to bend as a position of the closely-wound portion 52 covered with the outer tube 36, a second portion 182b whose bending difficulty is reduced linearly more than the first portion 182a, and a third portion 182c whose bending difficulty is made to coincide with the bending difficulty of a position of the second sparsely-wound region 46 covered with the outer tube 36. That is, here, the second portion 182b serves as a reduction portion that linearly reduces the bending difficulty of the third flexible portion 76.

Therefore, the bending difficulty of the third flexible portion 76 including the change portion 56 of the helical tube 32 as mentioned above coincides with the bending difficulty of the second flexible portion 74 at its distal end, and coincides with the bending difficulty of the fourth flexible portion 78 at its proximal end. In the above manner, the third flexible portion 76 positioned between the second flexible portion 74 and the fourth flexible portion 78, having a bending difficulty that is between the bending difficulties of the second flexible portion 74 and the fourth flexible portion 78, allows the change (difference) in the bending difficulty to be more gradual than in the case of arranging the fourth flexible portion 78 directly at the proximal end of the second flexible portion 74.

Therefore, when the user pushes the insertion section 12, that is, the flexible tube 26, further into the passage while holding the third flexible portion 76 and/or the fourth flexible portion 78, the third flexible portion 76 between the distal end of the fourth flexible portion 78 and the proximal end of the second flexible portion 74, and the distal end portion of the fourth flexible portion 78 itself can be prevented from being deflected (buckled). Therefore, the present modification capable of providing a flexible tube 26 which can be easily pushed into a winding passage, such as the large intestine, from a partly inserted state, and providing an insertion apparatus 10 having such a flexible tube 26.

Here the right contact force of the second portion 162b of the change portion 56 has been explained as being reduced linearly from the distal side towards the proximal side along the longitudinal axis L. In addition, for example, the tight contact force between adjacent parts of the wire member 32a may also be reduced in a curving manner.

In the following, a second modification of the first embodiment will be described using FIG. 6A and FIG. 6B.

Figure 6A:
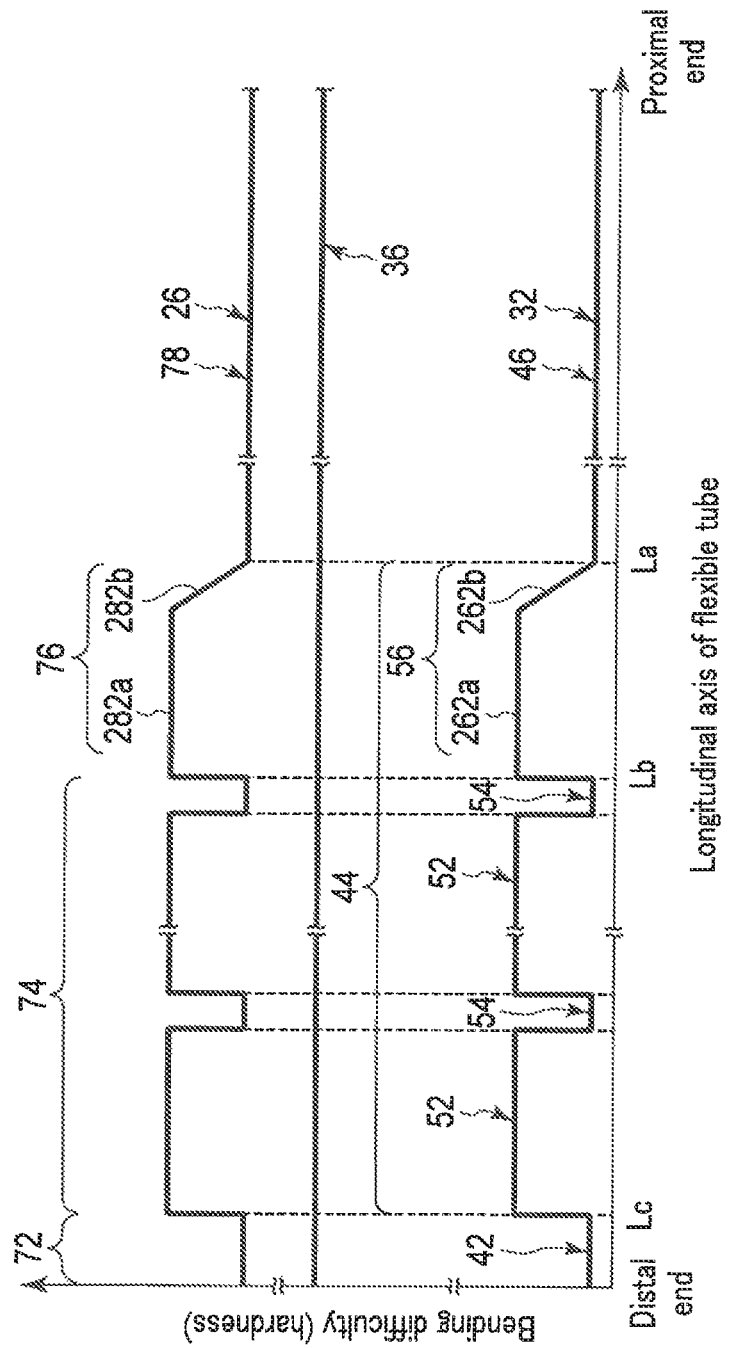
FIG. 6A is a schematic graph showing bending difficulties at positions along the longitudinal axis of the flexible tube, the helical tube, and the outer tube of the insertion section of the insertion apparatus according to a second modification of the first embodiment.
Figure 6B:
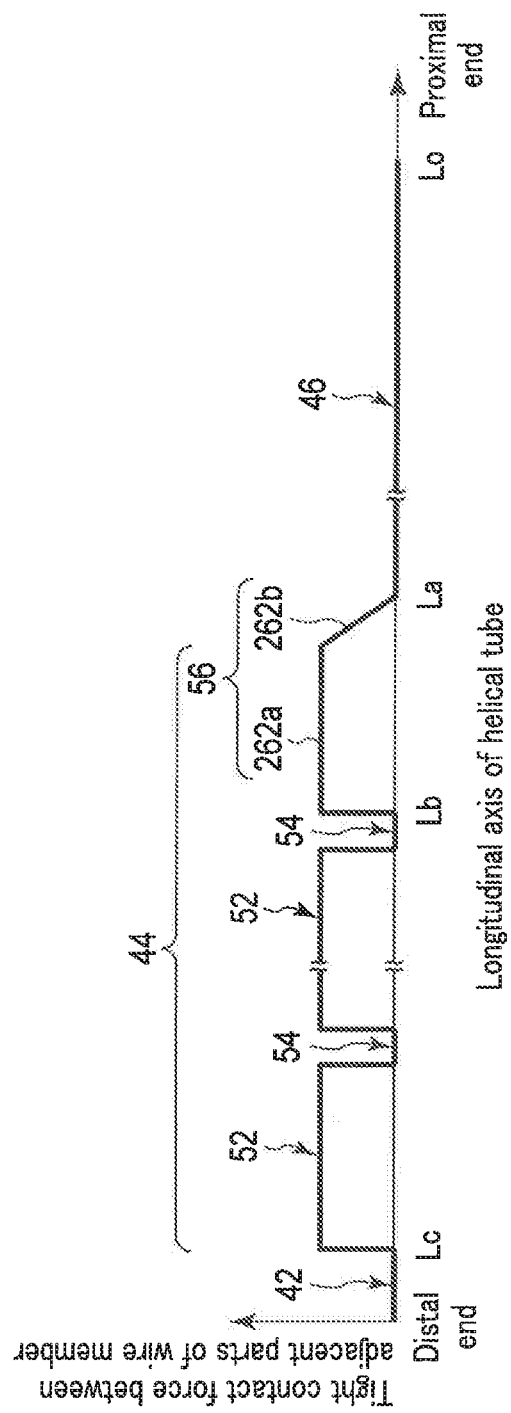
FIG. 6B is a schematic graph showing a tight contact force between the adjacent parts of the wire member at positions along the longitudinal axis of the helical tube of the flexible tube of the insertion section of the insertion apparatus according to the second modification of the first embodiment.

As shown in FIG. 6B, the distal end of the change portion 56 according to the present modification has the same tight contact force as the closely-wound portion 52 between the adjacent parts of the wire member 32a. The distal end of the change portion 56 includes a first portion 262a which maintains a state in which the tight contact force between the adjacent parts of the wire member 32a is constant. The proximal end of the change portion 56 includes a second portion 262b in which the tight contact force between the adjacent parts of the wire member 32a is reduced linearly towards its proximal end. Here, the second portion 262b serves as a reduction portion that reduces the bending difficulty of the change portion 56 linearly. That is, the tight contact force between the adjacent parts of the wire member 32a of the change portion 56 is gradually reduced in the second portion 262b. The position at the most proximal end of the change portion 56 has the same tight contact force as the second sparsely-wound region 46 (a state where the tight contact force is zero). That is, although the adjacent parts of the wire member 32a at the most proximal end of the change portion 56 contact each other, a tight contact force is not applied.

As shown in FIG. 6A, the thin flexible portion 76 including the change portion 56 of the helical tube 32 in the above manner includes, from its distal side towards its proximal side, a first portion 282a which is as difficult to bend as a position of the closely-wound portion 52 covered with the outer tube 36, and a second portion 282b whose bending difficulty is reduced linearly more than the first portion 282a and is made to coincide with the bending difficulty of a position of the second sparsely-wound region 46 covered with the outer tube 36. That is, here, the second portion 282b serves as a reduction portion that linearly reduces the bending difficulty of the second flexible portion 74.

Therefore, in the manner explained in the first embodiment, the present modification is capable of providing a flexible tube 26 which can be easily pushed into a winding passage, such as the large intestine, from a partly inserted state, and an insertion apparatus 10 having such a flexible tube 26.

As explained in the first modification, the second portion 262b may also reduce the tight contact force between the adjacent parts of the wire member 32a in a curving manner.

In the following, a third modification of the first embodiment will be described using FIG. 7A and FIG. 7B.

Figure 7A:
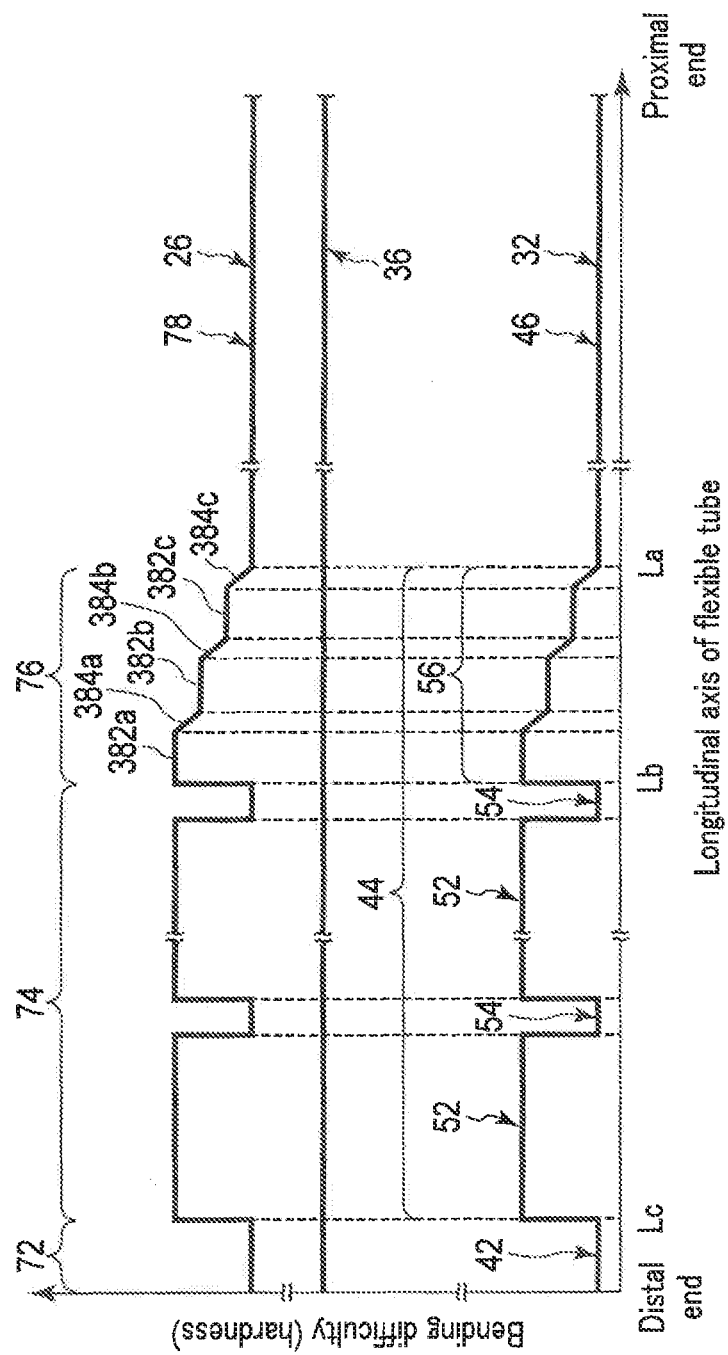
FIG. 7A is a schematic graph showing bending difficulties at positions along the longitudinal axis of the flexible tube, the helical tube, and the outer tube of the insertion section of the insertion apparatus according to a third modification of the first embodiment.
Figure 7B:
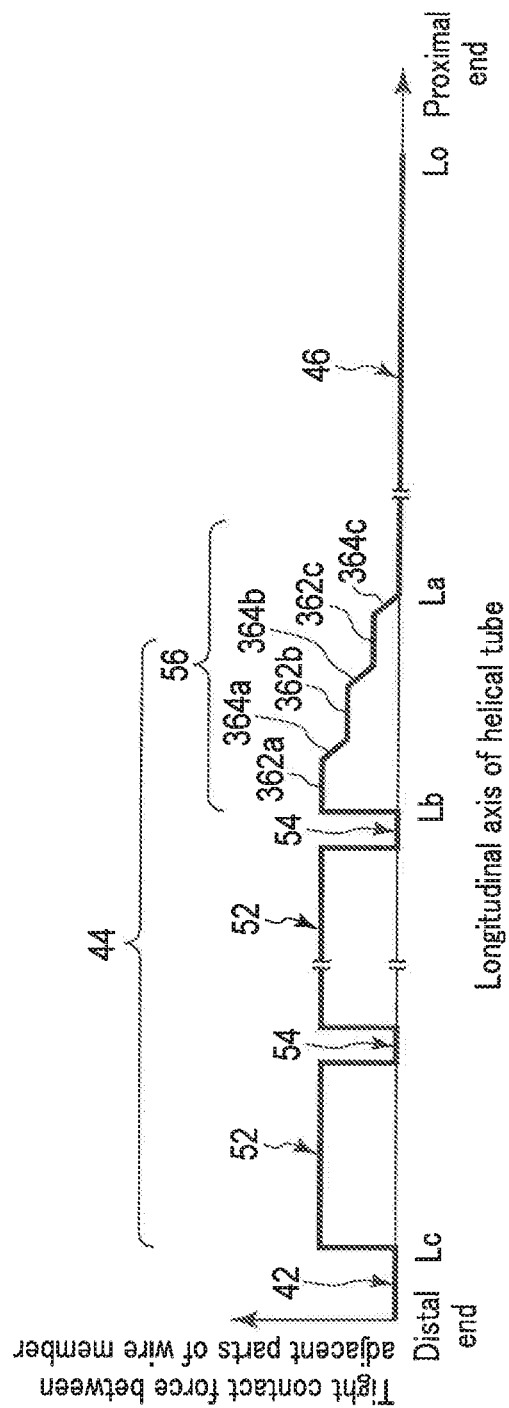
FIG. 7B is a schematic graph showing a tight contact force between the adjacent parts of the wire member at positions along the longitudinal axis of the helical tube of the flexible tube of the insertion section of the insertion apparatus according to the third modification of the first embodiment.

As shown in FIG. 7B, the distal end of the change portion 56 according to the present modification has the same tight contact force as the closely-wound portion 52 between the adjacent parts of the wire member 32a. The change portion 56 includes from the distal side towards the proximal side thereof, a first portion 362a having the same tight contact force as the closely-wound portion 52 between the wire member 32a, a second portion 362b maintaining a tight contact force between the adjacent parts of the wire member 32a constant in a state where the tight contact force is made lower than the first portion 362a, and a third portion 362c maintaining the tight contact force between the adjacent parts of the wire member 32a constant in a state where the tight contact force is made lower than the second portion 362b. The change portion 56 includes a first reduction portion 364a between the first portion 362a and the second portion 362b. The first reduction portion 364a reduces the tight contact force of the first portion 362a to the tight contact force of the second portion 362b. The change portion 56 includes a second reduction portion 364b between the second portion 362b and the third portion 362c. The second reduction portion 364b reduces the tight contact force of the second portion 362b to the tight contact force of the third portion 362c. The change portion 56 includes a third reduction portion 364c between the third portion 362c and the second sparsely-wound region 46. The third reduction portion 364c reduces the tight contact force of the third portion 362c to the tight contact force (a state in which the tight contact force is zero) of the second sparsely-wound region 46.

As shown in FIG. 7A, the third flexible portion 76 includes from its distal side towards its proximal side, a first constant portion 382a which is as difficult to bend as a position of the closely-wound portion 52 covered with the outer tube 36, a first change portion 384a whose bending difficulty is reduced linearly more than the first constant portion 382a, a second constant portion 382b which is as difficult to bend as a proximal end of the first change portion 384a, a second change portion 384b whose bending difficulty is reduced linearly more than the second constant portion 382b, a third constant portion 382c which is as difficult to bend as a proximal end of the second change portion 384b, and a third change portion 384c whose bending difficulty is reduced linearly more than the third constant portion 382c. That is, here, the first to third change portions 384a, 384b, and 384c serve as reduction portions that reduce the bending difficulty of the third flexible portion 76.

Therefore, the bending difficulty of the third flexible portion 76 including the change portion 56 of the helical tube 32 as mentioned above coincides with the bending difficulty of the second flexible portion 74 at its distal end and coincides with the bending difficulty of the fourth flexible portion 78 at its proximal end.

Therefore, as explained in the first embodiment or the above modifications, the present modification is capable of providing a flexible tube 26 which can be easily pushed into a winding passage, such as the large intestine, from a partly inserted state, and an insertion apparatus 10 including such a flexible tube 26.

Figure 8A:
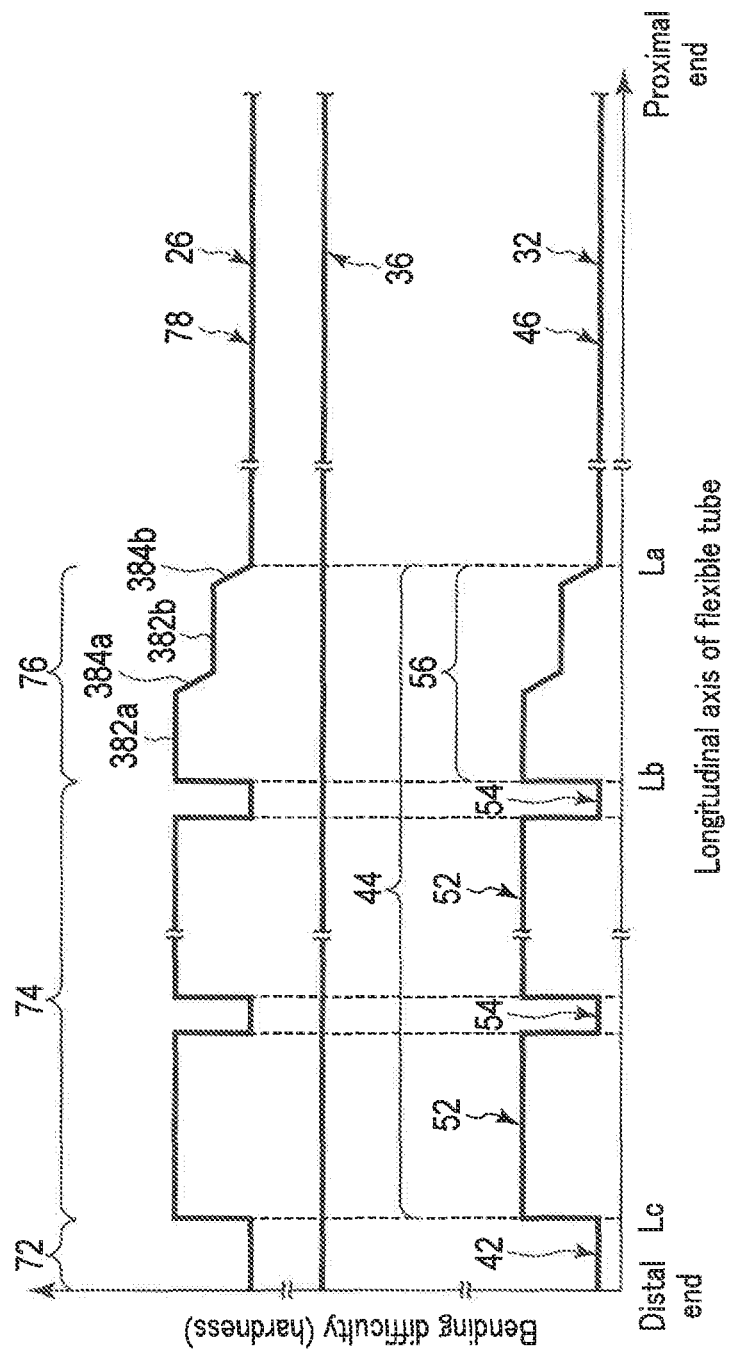
FIG. 8A is a schematic graph showing bending difficulties at positions along the longitudinal axis of the flexible tube, the helical tube, and the outer tube of the insertion section of the insertion apparatus according to a fourth modification of the first embodiment.

In the following, a fourth modification of the first embodiment will be explained using FIG. 8A and FIG. 8B.

Figure 8B:
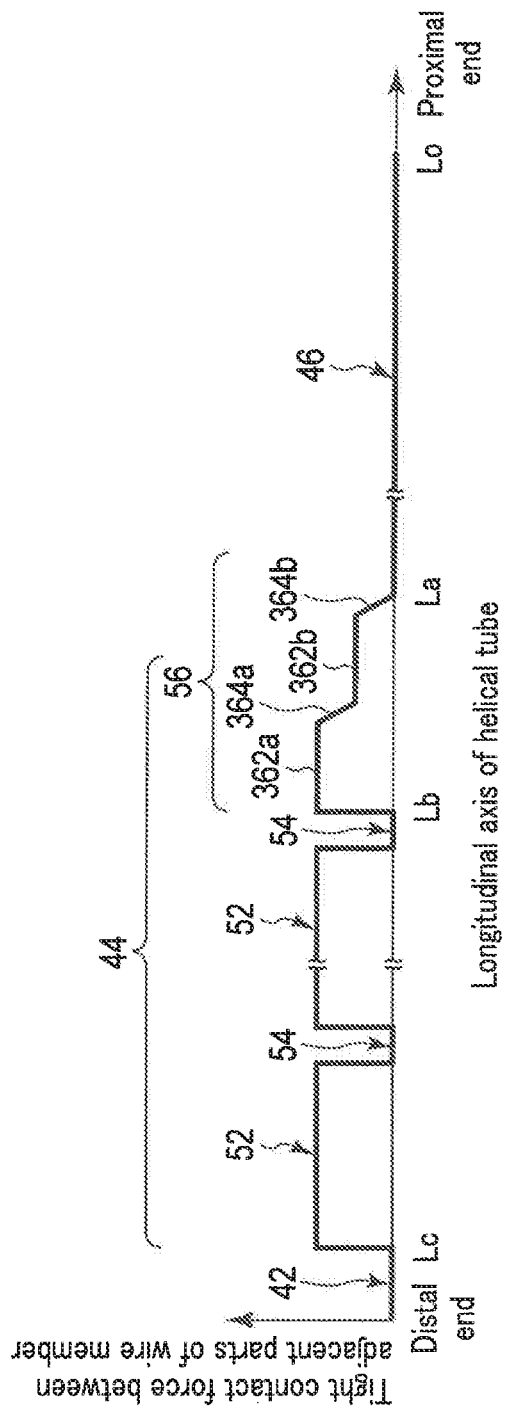
FIG. 8B is a schematic graph showing a tight contact force between the adjacent parts of the wire member at positions along the longitudinal axis of the helical tube of the flexible tube of the insertion section of the insertion apparatus according to the fourth modification of the first embodiment.

As shown in FIG. 8B, the change portion 56 according to the present modification includes the first portion 362a, the second portion 362b, the first reduction portion 364a, and the second reduction portion 364b explained in the third modification shown in FIG. 7B. That is, in the change portion 56 according to the present modification, the number of regions where the tight contact force is constant and the number of regions where the tight contact force is reduced are different from the third modification.

In the above manner, in the change portion 56, the tight contact force is reduced in stages from its distal side towards its proximal side so that the tight contact force of the change portion 56 approximates the tight contact force of the second sparsely-wound region 46 (a state in which the tight contact force is zero) from the state of having the same tight contact force as the closely-wound portion 52.

When the outer tube 36 that has a constant bending difficulty along the longitudinal axis L covers the outer side of such helical tube 32, the bending difficulty of the third flexible portion 76 is made to approximate the bending difficulty of the fourth flexible portion 78 from the bending difficulty of the second flexible portion 74 by reducing the bending difficulty stepwise to facilitate bending.

As explained above, the number of regions of the reduction portion and the number of regions where the tight contact force between the adjacent parts of the wire member 32a is constant in the helical tube 32 of the change portion 56 can be set as appropriate.

In the following, a fifth modification of the first embodiment will be explained using FIG. 9A and FIG. 9B. In the present modification, as a further modification of the first modification shown in FIG. 5A and FIG. 5B, an example of adjusting a bending difficulty of the outer tube 36 will be explained. The present modification may certainly be regarded as a further modification of the first embodiment shown in FIG. 4A and FIG. 4B, or shown in each of the modifications shown in FIG. 6A to FIG. 8B.

Figure 9A:
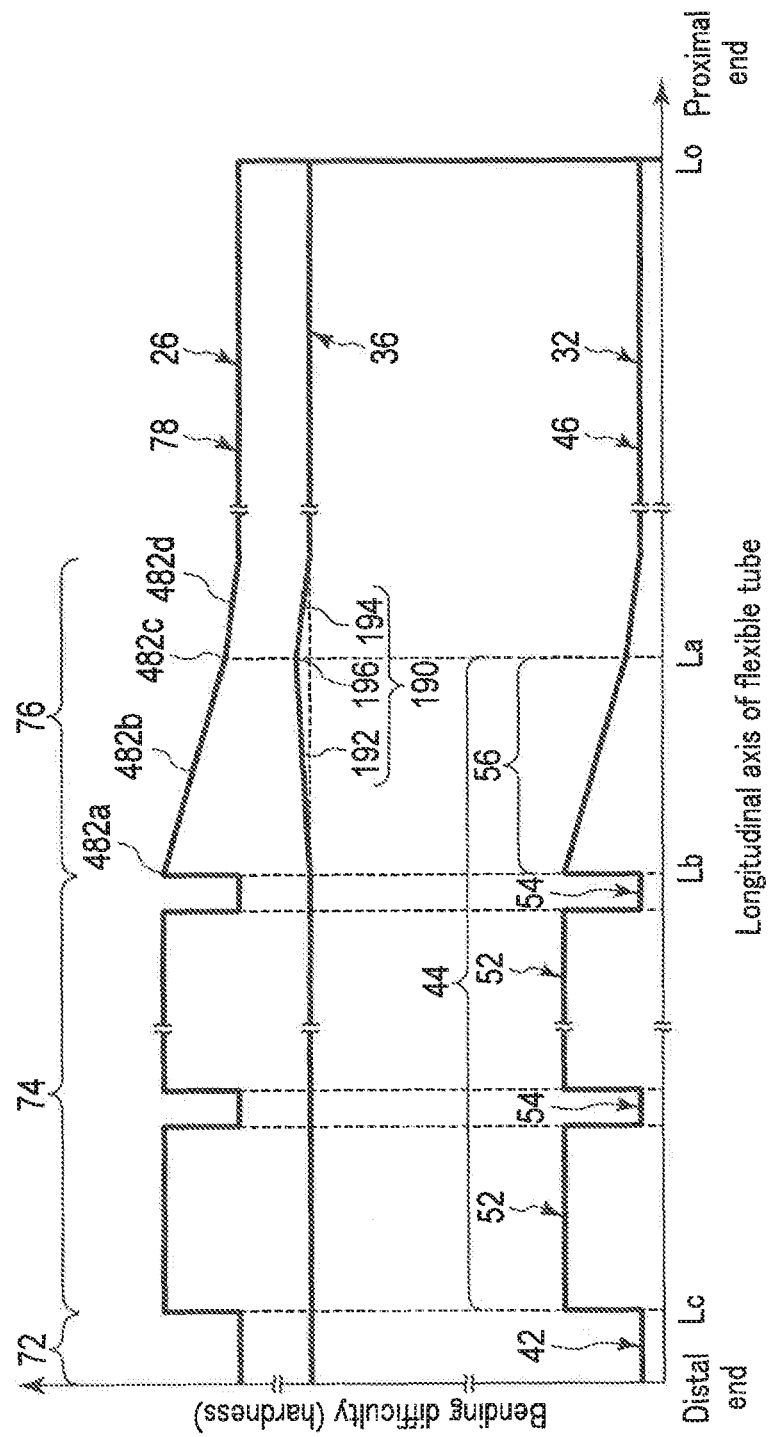
FIG. 9A is a schematic graph showing bending difficulties at positions along the longitudinal axis of the flexible tube, the helical tube, and the outer tube of the insertion section of the insertion apparatus according to a fifth modification of the first embodiment.
Figure 9B:
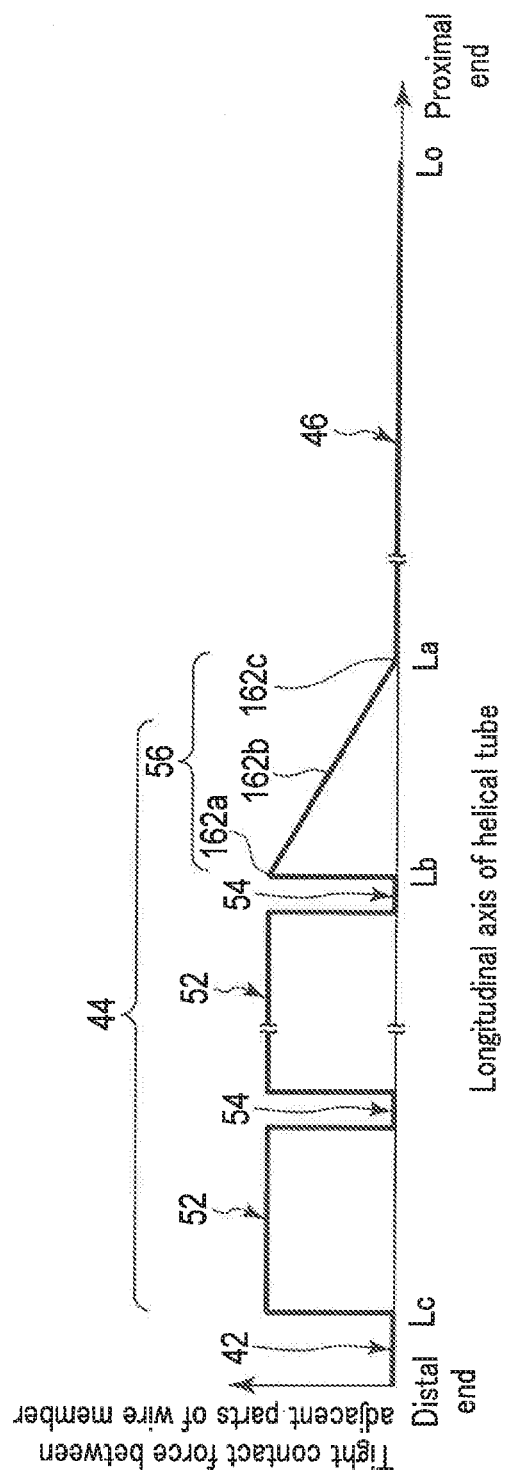
FIG. 9B is a schematic graph showing a tight contact force between the adjacent parts of the wire member at positions along the longitudinal axis of the helical tube of the flexible tube of the insertion section of the insertion apparatus according to the fifth modification of the first embodiment.

As shown in FIG. 9A, the outer tube 36 according to the present modification has a constant bending difficulty at the first and second flexible portions 72 and 74; however, the outer tube 36 has a bending difficulty that is changed along the longitudinal axis L at the third flexible portion 76. That is, the outer tube 36 according to the present modification includes an adjusting portion 190 that adjusts the bending difficulty (bending easiness) at the third flexible portion 76 (at least in the range between length Lb and length La from the distal end 26a). Specifically, the outer tube 36 includes an adjusting portion 190 for adjusting the bending easiness of the flexible tube 26 on the outer side of the boundary between the change portion 56 and the sparsely-wound region 46. In the present modification, the third flexible portion 76 is considered as including not only the change portion 56, but also the distal end portion of the second sparsely-wound region 46.

In the present modification, the adjusting portion 190 includes a rising portion 192 that increases the bending difficulty of the outer tube 36 itself as the tight contact force of the change portion 56 of the helical tube 32 is gradually reduced towards the proximal end, and a reduction portion 194 which gradually reduces the bending difficulty of the outer tube 36 itself towards the proximal side (gradually increases the bending easiness towards the proximal end).

At the adjusting portion 190, for example, the bending difficulty of the outer tube 36 on the distal side of the third flexible portion 75 is gradually increased from the distal side towards the proximal side along the longitudinal axis L. On the other hand, at the adjusting portion 190, the bending easiness of the outer tube 36 on the proximal side of the third flexible portion 76 is gradually increased from the distal side towards the proximal side along the longitudinal axis L. A point of change 196 is at the boundary of the rising portion 192 and the reduction portion 194 of the adjusting portion 190.

As shown in FIG. 9A, the third flexible portion 76 of the present modification includes, from its distal side towards its proximal side, a first portion 482a which is as difficult to bend as a position of the closely-wound portion 52 covered with the outer tube 36, a second portion 482b whose bending difficulty is reduced linearly more than the first portion 482a, a third portion 482c whose bending difficulty is changed between its distal side and proximal side by the point of change 196 of the outer tube 36, and a fourth portion 482d whose bending difficulty is reduced linearly more than the third portion 482c. Here, the fourth portion 482d is inclined more gradually than the second portion 482b.

That is, the adjusting portion 190 of the outer tube 36 cooperates with the change portion 56 of the helical tube 32 and adjusts the reduction rate of the bending difficulty at a position where the outer tube 36 covers the change portion 56 from its distal side towards its proximal side, to approximate the bending difficulty of the flexible portion 76 where the closely-wound portion 52 is covered with the outer tube 36 to the bending difficulty of another flexible portion 78 where the sparsely-wound region 46 is covered with the outer tube 36.

In addition to the tight contact force between the adjacent parts of the wire member 32a of the change portion 56 of the helical tube 32 in the second flexible portion 74, by adjusting the bending difficulty (bending easiness) of the outer tube 36 by the adjusting portion 190, the difference in the bending difficulty in the vicinity of the boundary between the proximal end of the second flexible tube 74 and the distal end of the third flexible portion 76 can be made even more gradual. Therefore, the third flexible portion 76 itself and the distal end portion of the fourth flexible portion 78 can be suppressed from deflecting.

Therefore, in the manner explained in the first embodiment, the present modification is capable of providing a flexible tube 26 which can be easily pushed into a winding passage, such as the large intestine, from a partly inserted state, and an insertion apparatus 10 having such a flexible tube 26.

In the following, a second embodiment will be explained using FIG. 10A to FIG. 10C. The present embodiment is a modification of the first embodiment which includes each modification, in which, to omit detailed explanations, the same symbols as those in the first embodiment will be applied whenever possible to the same members or the members with the same functions as those explained in the first embodiment.

Figure 10C:
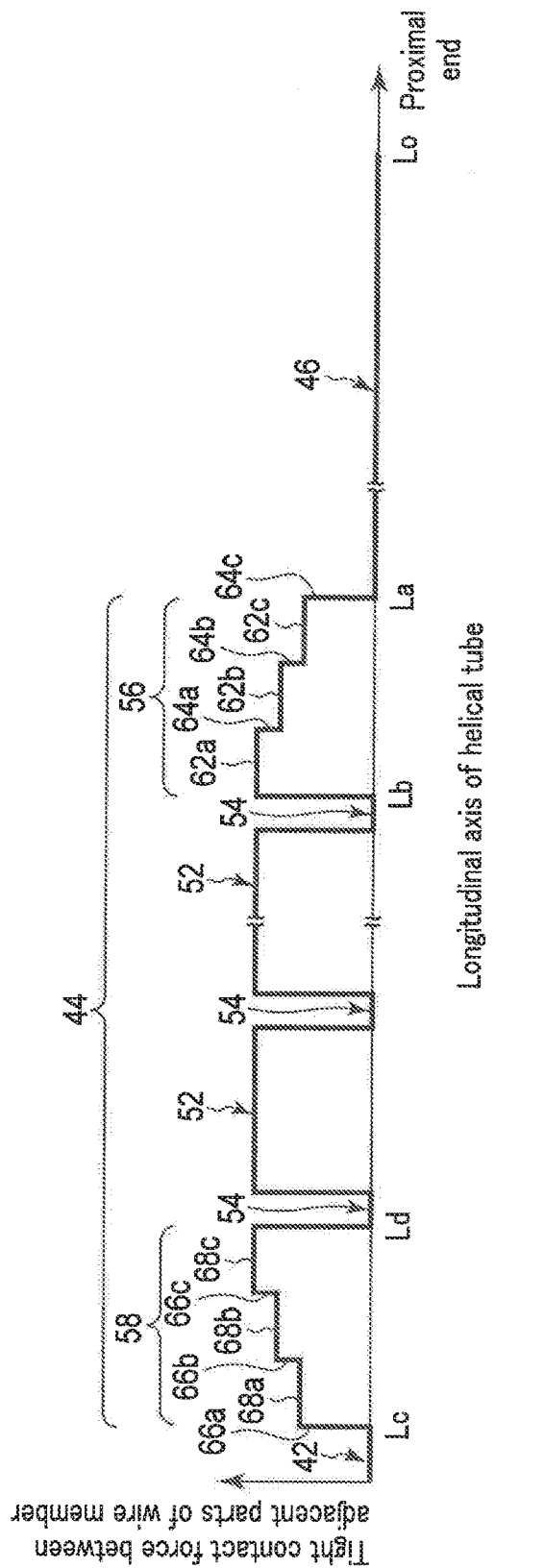
FIG. 10C is a schematic graph showing a tight contact force between the adjacent parts of the wire member at positions along the longitudinal axis of the helical tube of the flexible tube of the insertion section of the insertion apparatus according to the second embodiment.

As shown in FIG. 10C, the closely-wound region 44 of the helical tube 32 according to the present embodiment includes, in addition to the change portion (first change portion) 56 explained in the first embodiment, another second tight contact force change portion 58. The sparsely-wound portion (second sparsely-wound portion) 54 is arranged at the distal side of the closely-wound portion 52 located at the most distal end, and the second change portion 58 is arranged at the distal side of the sparsely-wound portion 54. The first sparsely-wound region 42 is arranged consecutively at the distal side of the second change portion 58.

The second change portion 58 is at the distal side of the closely-wound region 44. Specifically, at least one closely-wound portion 52 and at least two sparsely-wound portions 54 are arranged between the second change portion 58 and the first change portion 56. It is desirable that the length of at least one closely-wound portion 52 along the longitudinal axis L is longer than the length of the second tight contact force change portion 58 along the longitudinal axis L.

As shown in FIG. 10A, it is assumed that the distal end of the second change portion 58 is positioned at length Lc (<Lb<La<Lo), and that the proximal end of the second change portion 58 is positioned at length Ld (Lc<Ld>Lb>La>Lo) along the longitudinal axis L from the distal end 26a of the flexible tube 26.

As shown in FIG. 10B, the second change portion 58 of the closely-wound region 44 of the helical tube 32 and the outer tube 36 on the outer side of the closely-wound region 44 cooperate with each other to form a fifth flexible portion 76a. The fifth flexible portion 76a is formed between the first flexible portion 72 and the second flexible portion 74.

As shown in FIG. 10C, in the present embodiment, the tight contact force between the adjacent parts of the wire member 32a in the second change portion 58 is made to increase gradually along the longitudinal axis L from the distal side towards the proximal side, which is the opposite of the case of the first change portion 56. Specifically, the second change portion 58 includes, from its distal side towards its proximal side, a first rising portion 66a which increases the tight contact force from the tight contact force of the first sparsely-wound region 42 (a state where the tight contact force is zero), a first portion 68a which maintains a state in which the tight contact force between the adjacent parts of the wire member 32a increased at the first rising portion 66a is lower than the closely-wound portion 52 constant, a second rising portion 66b which increases the tight contact force of the first portion 68a, a second portion 68b which maintains a state in which the tight contact force between the adjacent parts of the wire member 32a increased at the second rising portion 66b is lower than the closely-wound portion 52 constant, a third rising portion 66c which increases the tight contact force of the second portion 68b, and a third portion 68c which has the same tight contact force as that of the closely-wound portion 52, increased at the third rising portion 66c.

In the above manner, in the second change portion 58 of the helical tube 32, the tight contact force between the adjacent parts of the wire member 32a is increased in stages from its distal side towards its proximal side so that the tight contact force is approximated to a state of having the same tight contact force as the tight contact force between the adjacent parts of the wire member 32a of the closely-wound portion 51 at its proximal end.

Therefore, as shown in FIG. 10B, the fifth flexible portion 76a of the flexible tube 26 obtained by covering the above helical tube 32 with the outer tube 36 includes between the length Lc and the length Ld from the distal end 26a, a first rising portion 86a which increases the bending difficulty and the resiliency from those in a state where the sparsely-wound portion 54 is covered with the outer tube 36, a first portion 88a which maintains the bending difficulty and the resiliency increased at the first rising portion 86a constant, a second rising portion 86b which increases the bending difficulty and the resiliency of the first portion 88a, a second portion 88b which maintains the bending difficulty and the resiliency increased at the second rising portion 86b constant, a third rising portion 86c which increases the bending difficulty and the resiliency of the second portion 88b to the bending difficulty and the resiliency of a state where the closely-wound portion 52 is covered with the outer tube, and a third portion 88c which maintains the bending difficulty and the resiliency increased at the rising portion 86c constant and has the same bending difficulty and resiliency as a portion where the closely-wound portion 52 is covered with the outer tube 36.

In this manner, the fifth flexible portion 76a at a position between the position of the length Lc and the position of the length Ld from the distal end 26a has the bending difficulty and the resiliency gradually approximated to the second flexible portion 74 as it transitions from its distal side towards its proximal side. That is, the resiliency is gradually increased from the distal end towards the proximal end of the fifth flexible portion 76a.

The bending difficulty and the resiliency of the outer tube 36 of the fifth flexible portion 76a may also be adjusted as in the adjusting portion 190 of the fifth modification of the first embodiment. That is, the outer tube 36 and the second change portion 58 may cooperate with each other to adjust the bending difficulty and the resiliency of the fifth flexible portion 76a.

Since the structure of the second flexible portion 74 was explained in the first embodiment including each of the modifications, explanations will be omitted here.

In the following, the operation of the insertion apparatus 10 of the present embodiment will be explained.

The user of the insertion apparatus 10 grips the fifth flexible portion 76a and/or the second flexible portion 74 of the flexible tube 26. Then, the user inserts the insertion section 12 into an appropriately curved and narrow passage, such as from an anus to a transverse colon of a large intestine, in the order of the distal rigid portion 22, the bending portion 24, and the flexible tube 26. The user changes the held positions of the flexible tube 26 gradually towards the proximal side to allow the insertion section 12 to be inserted further into the passage.

As the insertion section 12 is inserted into the passage, an external force (including a force of gravity) is applied from the inner circumferential surface of the passage to the first flexible portion 72, the fifth flexible portion 76a, and the second flexible portion 74 from a direction departing from the direction along the longitudinal axis L of the flexible tube 26 (for example, a perpendicular direction). In the case where the external force applied to the fifth flexible portion 76a is smaller than the bending difficulty of the fifth flexible portion 76a, the fifth flexible portion 76a is not deflected and maintains a linear state.

In the case where the external force (including a force of gravity) applied from the inner circumference surface of the passage is equal to or larger than the bending difficulty of the fifth flexible tube 76a, the fifth flexible tube 76a will start deflecting from the essentially linear state. That is, the fifth flexible portion 76a will be bent from an essentially linear state. Since the second flexible portion 74 is formed to be bent appropriately by the external force from the passage such as the large intestine, and the fifth flexible portion 76a is formed to be bent easier after the first flexible portion 72, the large intestine may be prevented from receiving an excessive load. The bending difficulty at the fifth flexible portion 76a is gradually increased from the distal side to the proximal side thereof, thereby allowing the fifth flexible portion 76a to make the difference in bending easiness gradual between the first flexible portion 72 and the second flexible portion 74. Therefore, in the case where the first flexible portion 72 is bent by an external force, the fifth flexible portion 76a is also bent easily by the external force.

The fifth flexible portion 76a has a higher resiliency than the first flexible portion 72. Therefore, the fifth flexible portion 76a more easily returns to the approximately straight state from the bent state in comparison with the first flexible portion 72. That is, even if the fifth flexible portion 76a is bent at any position thereof, the tight contact force applied between the adjacent parts of the wire member 32a in the closely-wound region 44 of the fifth flexible portion 76a allows the fifth flexible portion 76a to easily return to the approximately straight state.

For example, in the case of inserting the distal portion 12a of the insertion section 12 into the passage from, for example, the anus to a deep part of the large intestine, since the first flexible portion 72 can be easily bent, it can be easily bent appropriately along the inner circumference of the passage. Thus, the insertion section 12, including the first flexible portion 72, the fifth flexible portion 76a, and the second flexible portion 74, bends along the curve of the flexible passage such as the large intestine. Because of the resiliency, the fifth flexible portion 76a and the second flexible portion 74 can be returned easily to the approximately straight state from the bent state. Therefore, after the first flexible portion 72 passes a curve of the passage, the fifth flexible portion 76a and the second flexible portion 74 utilize their resiliency to make the curved portion of the passage essentially linear. In this manner, the distal end 12a of the insertion section 12 can be inserted into a deep part of the passage.

The bending difficulty of the fifth flexible portion 76a changes gradually from the first flexible portion 72 up to the second flexible portion 74. Therefore, when the user pushes the distal end of the insertion section 12 further into the large intestine by gripping the second flexible portion 74, the force acting on the second flexible portion 74 is unfailingly transmitted to the first flexible portion 72 through the fifth flexible portion 76a. At this time, when an external force exceeding the bending difficulty is applied to the fifth flexible portion 76a, the fifth flexible portion 76a is bent appropriately.

In a similar manner, when the user pushes the distal end of the insertion section 12 further into the large intestine by gripping the third flexible portion 76 and/or the fourth flexible portion 78, the force acting on the third flexible portion 76 and/or the fourth flexible portion 78 is unfailingly transmitted to the first flexible portion 72 through the third flexible portion 76, the second flexible portion 74 and the fifth flexible portion 76a.

As explained above, the insertion apparatus 10 according to the present embodiment may be considered as follows.

By arranging the fifth flexible portion 76a consecutively between the proximal end of the first flexible portion 72 and the distal end of the second flexible portion 74, a drastic change in the bending difficulty between the first flexible portion 72 and the distal end of the second flexible portion 74 would not be produced. Therefore, when inserting the distal end 12a of the insertion section 12 further along the passage, the flexible tube 26 is appropriately bent at the vicinity of the boundary between the first flexible portion 72 and the second flexible portion 74 to prevent the passage from receiving a load to the greatest extent possible. The resiliency of the fifth flexible portion 76a and the second flexible portion 74 allows the curved passage to be returned easily to the approximately straight state. Therefore, after the first flexible portion 72 passes a curve of the passage, the fifth flexible portion 76a and the second flexible portion 74 utilize their resiliency to make the curved portion of the passage essentially linear. In this manner, the distal end 12a of the insertion section 12 can be inserted into a deep part of the passage.

The fifth flexible portion 76a of the present embodiment has been explained as having the bending difficulty increased stepwise from the distal side towards the proximal side, which is the opposite of the case of the third flexible portion 76. Furthermore, the bending difficulty of the fifth flexible portion 76a may also be made to increase linearly from the distal side towards the proximal side. Each of the first to third rising portions 86a, 86b, and 86c is made to increase the bending difficulty drastically; however, the number of rising portions may be further increased so as to make the bending difficulty increase more gradually.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube in a unbent state and not subject to external stress, the flexible tube comprising:
a helical tube which defines a longitudinal axis by a distal end and a proximal end of the helical tube, the helical tube being formed by a winding wire member, the helical tube including:
a closely-wound region including:
first adjacent parts of the wire member that are adjacent and closely attached along the longitudinal axis, the first adjacent parts applying contact forces between each other along the longitudinal axis,
second adjacent parts of the wire member that are arranged on a proximal side of the first adjacent parts, the second adjacent parts being adjacent and separated from each other along the longitudinal axis, and
third adjacent parts of the wire member that are arranged on a proximal side of the second adjacent parts, the third adjacent parts being adjacent and in close contact with one another along the longitudinal axis, the third adjacent parts applying contact forces between each other along the longitudinal axis, wherein the contact forces of a proximal side of the third adjacent parts along the longitudinal axis are lower than the contact forces of a distal side of the third adjacent parts along the longitudinal axis, and the contact forces of the proximal side of the third adjacent parts are lower than the contact forces of the first adjacent parts; and
a sparsely-wound region including fourth adjacent parts of the wire member which are arranged on the proximal side of the third adjacent parts, the fourth adjacent parts being adjacent and separated from each other along the longitudinal axis; and
a cylindrical outer tube which covers an outer side of the helical tube across an entire length of the helical tube, the cylindrical outer tube defining the length of the helical tube, the cylindrical outer tube including an adjuster arranged on an outer side of a boundary between the third adjacent parts of the closely-wound region and the fourth adjacent parts of the sparsely-wound region, the adjuster being configured to adjust a bending stiffness of the cylindrical outer tube.

2. The flexible tube according to claim 1, wherein the closely-wound region includes:
fifth adjacent parts of the wire member which are arranged on a distal side of the first adjacent parts, the fifth adjacent parts being adjacent to and separated from each other along the longitudinal axis; and
sixth adjacent parts of the wire member which are arranged continuously on a distal side of the fifth adjacent parts, the sixth adjacent parts being adjacent and closely attached along the longitudinal axis, the sixth adjacent parts applying contact forces between each other along the longitudinal axis.

3. The flexible tube according to claim 1, wherein:
a distal end portion of the third adjacent parts includes a portion having constant contact forces, each of the constant contact forces being equal to or lower than each of the contact forces of the first adjacent parts; and
a proximal end portion of the third adjacent parts includes a portion having contact forces that are each equal to or lower than each of the constant contact forces of the portion of the distal end portion of the third adjacent parts.

4. The flexible tube according to claim 1, wherein a length of the first adjacent parts along the longitudinal axis is longer than a length of the third adjacent parts along the longitudinal axis.

5. The flexible tube according to claim 1, wherein:
the first adjacent parts, the second adjacent parts, and the cylindrical outer tube form a first flexible portion;
the third adjacent parts and the cylindrical outer tube form a second flexible portion;
the fourth adjacent parts of the sparsely-wound region and the cylindrical outer tube form a third flexible portion;
a bending difficulty of a distal end of the second flexible portion is configured to gradually change a bending difficulty of a proximal end of the first flexible portion along the longitudinal axis; and
a bending difficulty of a proximal end of the second flexible portion is configured to gradually change a bending difficulty of a distal end of the third flexible portion along the longitudinal axis.

6. The flexible tube according to claim 1, wherein:
the closely-wound region includes:
fifth adjacent parts which are arranged on a distal side of the first adjacent parts, the fifth adjacent parts being adjacent to and separated from each other along the longitudinal axis, and
sixth adjacent parts which are arranged on a distal side of the fifth adjacent parts, the sixth adjacent parts being adjacent to each other and closely attached along the longitudinal axis, the sixth adjacent parts applying contact forces between each other along the longitudinal axis;
the contact forces of a distal side of the sixth adjacent parts along the longitudinal axis are lower than the contact forces of a proximal side along the longitudinal axis within the sixth adjacent parts;
the contact forces of the distal side of the sixth adjacent parts are lower than the contact forces of the first adjacent parts; and
the helical tube includes a second sparsely-wound region including seventh adjacent parts of the wire member which are arranged on a distal side of the sixth adjacent parts, the seventh adjacent parts being adjacent to and separated from each other along the longitudinal axis.

7. The flexible tube according to claim 6, wherein a length of the first adjacent parts along the longitudinal axis is longer than a length of the second sparsely-wound region along the longitudinal axis.

8. The flexible tube according to claim 1, further comprising a braid which is arranged between the helical tube and the cylindrical outer tube.

9. The flexible tube according to claim 1, wherein:
the first adjacent parts, the second adjacent parts, and the cylindrical outer tube form a first flexible portion;
the third adjacent parts and the cylindrical outer tube form a second flexible portion;
the fourth adjacent parts of the sparsely-wound region and the cylindrical outer tube form a third flexible portion;
the contact force within the third adjacent parts is gradually decreased towards the proximal side of the third adjacent parts;
the adjuster of the cylindrical outer tube includes:
an increasing portion which is configured to increase a bending difficulty of the cylindrical outer tube towards the proximal end of the cylindrical outer tube as the contact forces within the third adjacent parts are gradually decreased over distance towards the proximal side of the third adjacent parts, and
a decreasing portion which is arranged on a proximal side of the increasing portion, the decreasing portion being configured to gradually decrease the bending difficulty of the cylindrical outer tube towards the proximal end of the outer tube as the contact forces within the third adjacent parts are gradually decreased over distance towards the proximal side of the third adjacent parts; and
the adjuster changes properties over a longitudinal distance at a position of the adjuster such that a bending difficulty of the adjuster in the second flexible portion decreases from a bending difficulty equivalent to a bending difficulty of the first flexible portion, to a bending difficulty equivalent to a bending difficulty of the third flexible portion.

10. An insertion apparatus comprising:
an insertion section including:
a distal rigid portion;
a bending portion providing on a proximal side of the distal rigid portion, the bending portion being configured to be bent; and
the flexible tube according to claim 1 provided on a proximal side of the bending portion.

* * * * *